United States Patent [19]
Ross et al.

[11] Patent Number: 5,205,819
[45] Date of Patent: Apr. 27, 1993

[54] PUMP APPARATUS FOR BIOMEDICAL USE

[75] Inventors: Calvin J. Ross, Suffolk; Victor C. Humberstone, Cambridge; Richard J. Warby, Wisbech, all of United Kingdom

[73] Assignee: Bespak PLC, Norfolk, United Kingdom

[21] Appl. No.: 813,756

[22] Filed: Dec. 30, 1991

Related U.S. Application Data

[63] Continuation-in-part of Ser. No. 520,191, May 9, 1990, abandoned.

[30] Foreign Application Priority Data

May 11, 1989 [GB] United Kingdom ............... 8910843
Nov. 21, 1989 [GB] United Kingdom ............... 8926314
Jan. 25, 1991 [GB] United Kingdom ............... 9101648

[51] Int. Cl.$^5$ ............................................. A61M 1/00
[52] U.S. Cl. ............................ 604/67; 128/DIG. 12; 417/413; 604/153
[58] Field of Search ............... 604/67, 152, 153; 128/DIG. 12, DIG. 13; 417/322, 413

[56] References Cited

U.S. PATENT DOCUMENTS

| | | |
|---|---|---|
| 3,425,415 | 2/1969 | Gordon et al. . |
| 3,963,380 | 6/1976 | Thomas, Jr. et al. . |
| 4,255,088 | 3/1981 | Newton et al. . |
| 4,344,743 | 9/1992 | Bessman et al. ............ 417/317 |
| 4,456,009 | 6/1984 | Vcelka et al. . |
| 4,486,190 | 12/1984 | Reinicke ..................... 604/67 |
| 4,487,601 | 12/1984 | Lindemann ................. 604/67 |
| 4,519,792 | 5/1985 | Dawe ..................... 128/DIG. 12 |
| 4,541,429 | 9/1985 | Prosl . |
| 4,565,500 | 1/1986 | Jeensalute et al. ........... 604/67 |
| 4,594,058 | 6/1986 | Fishell ....................... 604/153 |
| 4,596,575 | 6/1986 | Rosenberg et al. ........ 128/DIG. 12 |
| 4,650,469 | 3/1987 | Berg et al. ................. 604/153 |
| 4,655,766 | 4/1987 | Theeuwes et al. . |
| 4,657,490 | 4/1987 | Abbott ....................... 604/153 |
| 4,670,006 | 6/1987 | Sinnett et al. .............. 604/67 |
| 4,676,776 | 6/1987 | Howson .................... 128/DIG. 12 |
| 4,684,368 | 8/1987 | Kenyon ..................... 604/152 |
| 4,747,828 | 5/1988 | Tseo . |
| 4,758,228 | 7/1988 | Williams .................. 128/DIG. 12 |
| 4,798,589 | 1/1989 | Tseo . |
| 4,826,482 | 5/1989 | Kamen ..................... 128/DIG. 13 |
| 4,829,448 | 5/1989 | Balding et al. . |
| 4,838,887 | 6/1989 | Idriss ....................... 128/DIG. 12 |
| 4,842,584 | 6/1989 | Pastrone ................... 604/153 |
| 4,874,359 | 10/1989 | White et al. .............. 128/DIG. 13 |

FOREIGN PATENT DOCUMENTS

| | | |
|---|---|---|
| 0025005 | 8/1980 | European Pat. Off. . |
| 0134614 | 8/1984 | European Pat. Off. . |
| 0182502 | 5/1986 | European Pat. Off. . |
| 0398583 | 11/1990 | European Pat. Off. . |
| 3515848 | 11/1985 | Fed. Rep. of Germany . |
| WO82/01997 | 6/1982 | PCT Int'l Appl. . |
| WO85/04813 | 11/1985 | PCT Int'l Appl. . |
| WO86/07268 | 12/1986 | PCT Int'l Appl. . |
| WO86/07269 | 12/1986 | PCT Int'l Appl. . |
| WO87/03342 | 6/1987 | PCT Int'l Appl. . |
| WO87/07218 | 12/1987 | PCT Int'l Appl. . |
| WO88/05314 | 7/1988 | PCT Int'l Appl. . |
| WO89/07199 | 8/1989 | PCT Int'l Appl. . |
| 1089436 | 11/1986 | United Kingdom . |

OTHER PUBLICATIONS

Spencer et al., "An Electronically Controlled Piezoelectric Insulin Pump and Valves," *IEEE Transactions on Sonics and Ultrasonics*, vol. SU-25, No. 3, May 1978, pp. 153–156.

Schubert et al., "An Implantable Artificial Pancreas," *Medical & Biological Engineering & Computing*, 1980, vol. 18, pp. 527–537.

*Primary Examiner*—Paul J. Hirsch
*Attorney, Agent, or Firm*—Beveridge, DeGrandi, Weilacher & Young

[57] ABSTRACT

An infusion pump includes a piezoelectric actuator located in a housing and operable to deflect a flexible wall of a detachable pump body. The pump body defines a chamber of variable volume with non-return inlet and outlet valves. The pump body is disposable and connected to the housing by a releasable connector which biases the wall into operative engagement with the transducer. The transducer is provided with sense electrodes to measure the amplitude of deflection which is used to trigger alarms indicating the presence of bubbles in the chamber or of occlusion.

28 Claims, 17 Drawing Sheets

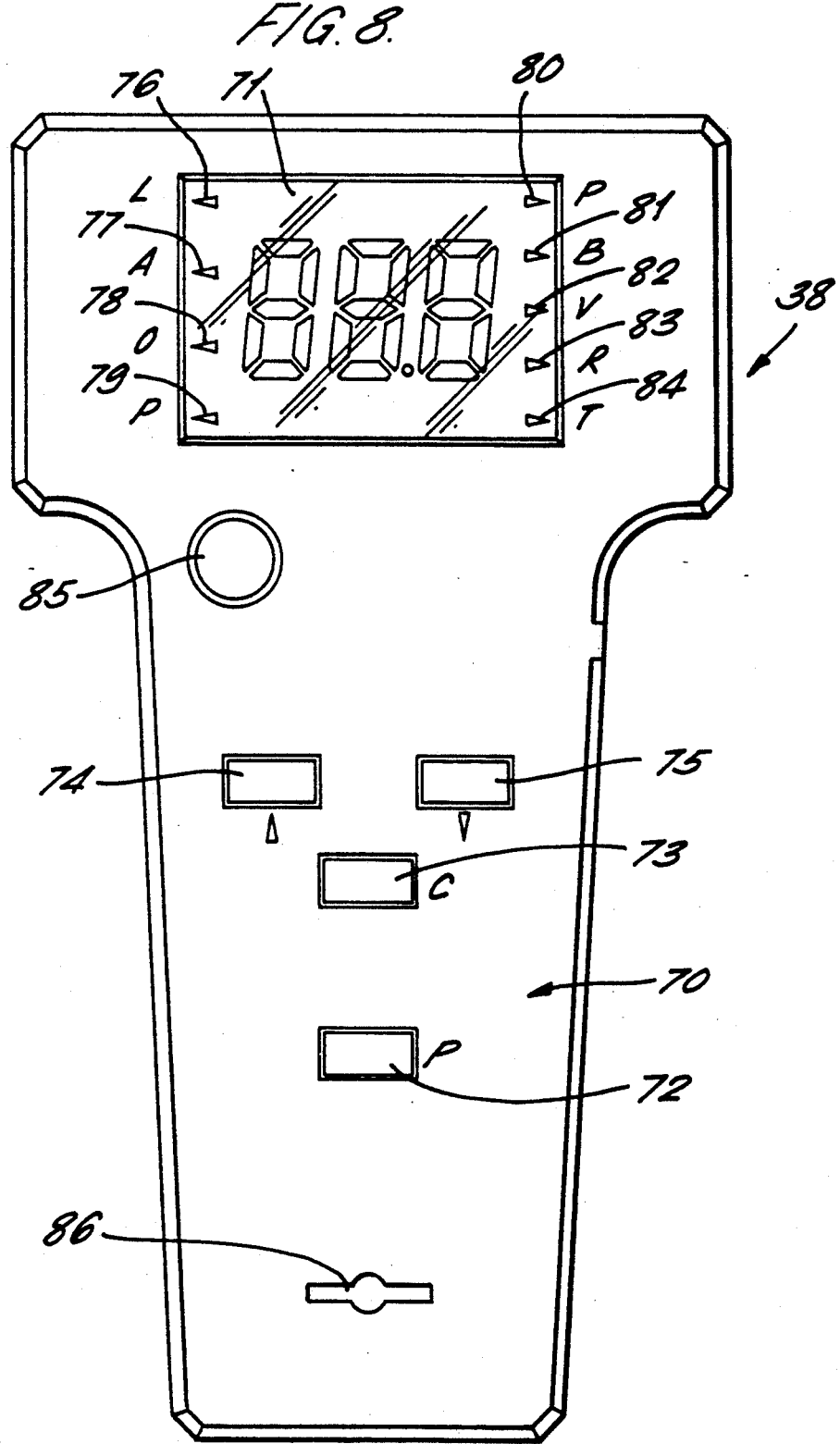

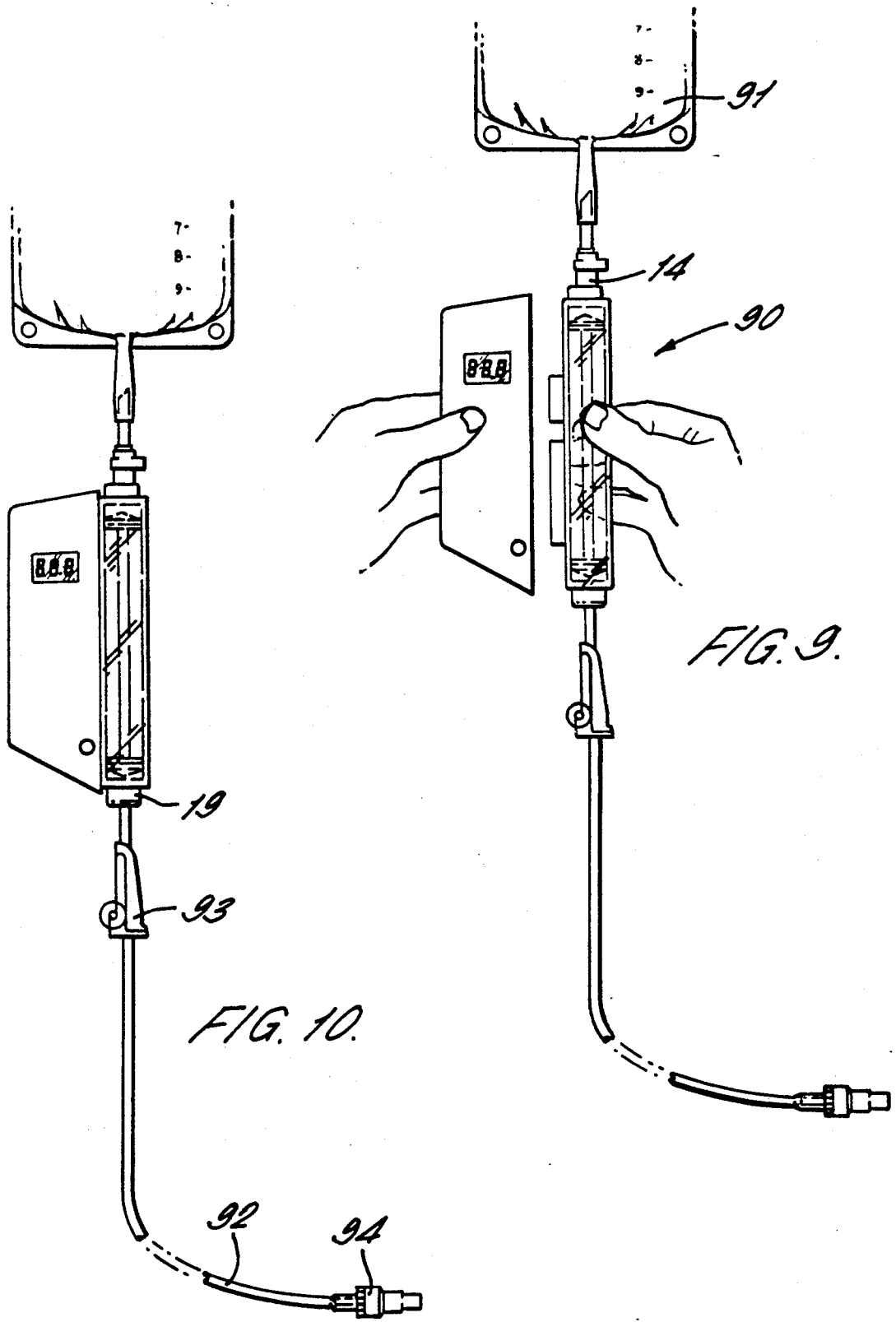

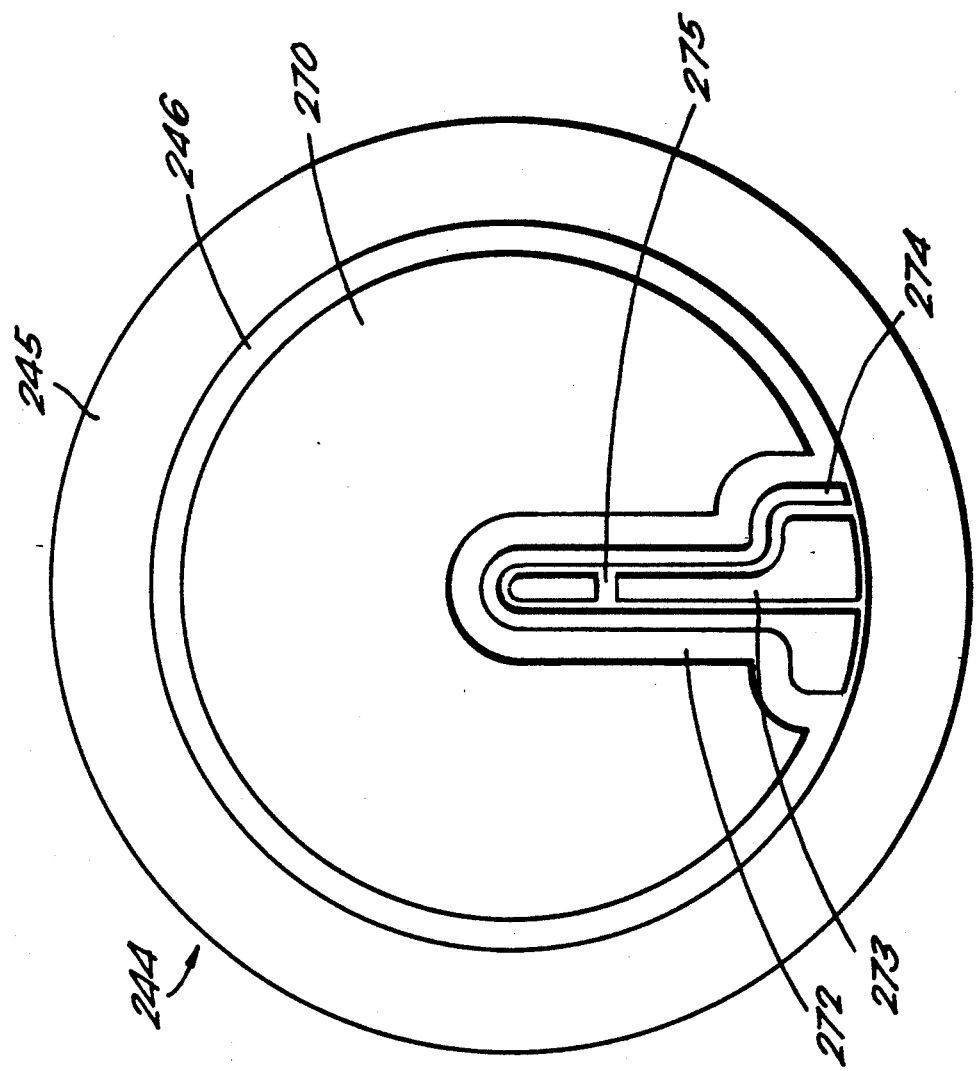
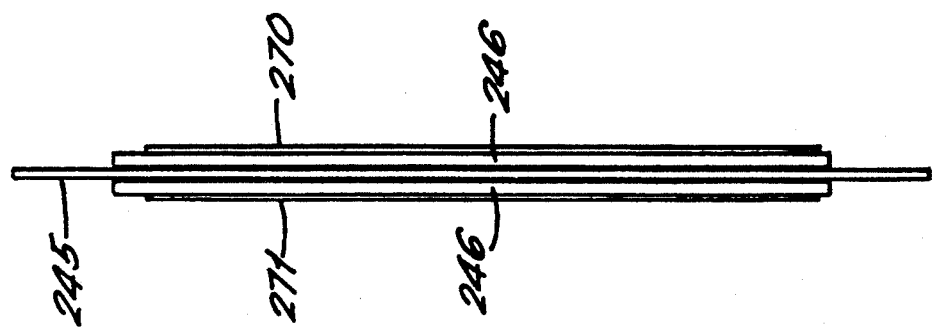

PUMP APPARATUS FOR BIOMEDICAL USE

This application is a continuation-in-part application from U.S. patent application No. 07/520191 filed May 9, 1990.

BACKGROUND OF THE INVENTION

This invention relates to pump apparatus for biomedical use and in particular but not exclusively for use in intravenous infusion of liquids to the human body or animal body.

Many medical procedures require the controlled introduction of liquids over a prolonged period into the human or animal body for example where a patient is to receive a drug, blood products, saline or nutrients etc at a controlled dose rate. Existing pump apparatus for such applications includes syringe pumps, drip monitors and peristaltic pumps each of which suffer the disadvantages of being expensive, complex to set up and operate and are generally inhibiting of patient movement. It is also known to introduce liquids into plants in a controlled manner in situations where it is inconvenient to have complex pump apparatus relying on external power supplies.

It has also been proposed in DE-2920975 for example to have a peristaltic pump within a housing which also contains means for controlling and actuating the pump so that the apparatus is self-contained and portable and may for example be attached to the body receiving an infusion.

A disadvantage of such peristaltic pumps is that the rate of flow at which liquid is delivered by the pump cannot be accurately controlled. Typically flow rate is measured by counting revolutions of the peristaltic roller mechanism and errors of up to 15% are typical in measured flow rate. A further difficulty is that, in the event of occlusion of the infusion flow path, known pumps and particularly syringe pumps are generally capable of building-up liquid pressure to a dangerous level. It is also difficult to effectively detect the presence of air bubbles within known pumps and typically a bubble detector relies on the use of sensors responsive to the difference in refractive index between air and the liquid being pumped. The presence of air bubbles is extremely dangerous during infusion and a disadvantage of known pumps is that any air bubble will easily pass through the pump.

It is also known from U.S. Pat. No. 4,596,575 to provide an implantable pump apparatus in which a pump chamber has a flexible wall movable by actuation of a piezoelectric transducer, the chamber having inlet and outlet valves which are electromagnetically actuated poppet valves. The pump is used to pump a buffer fluid which in turn pressurises a bag containing infusate. The infusate therefore does not pass through the pump chamber and the problems associated with bubble formation within the chamber are dealt with by ensuring that the buffer fluid is de-aerated before filling.

OBJECTS OF THE PRESENT INVENTION

It is an object of the present invention to provide pump apparatus particularly for infusion purposes which is simple and inexpensive to use and which is self-contained so as to allow patient movement during infusion.

It is a further object to provide pump apparatus and a method of pumping which avoids the danger of over pressurisation of infusate and which includes built-in safeguards against occlusion and bubble formation.

It is a further object to provide pump apparatus having a disposable pump body which allows a re-usable housing to be used with a fresh and sterile pump body for each infusion procedure.

SUMMARY OF THE INVENTION

According to the present invention there is disclosed a pump apparatus comprising, a pump body defining a pump chamber, an inlet duct communicating between the pump chamber and a source of a liquid to be pumped whereby, in use, the liquid fills the pump chamber, an outlet duct communicating with the chamber for the delivery of the liquid when pumped, actuating means operable to vary the volume of the pump chamber by movement of a flexible wall of the pump chamber to pump the liquid therefrom, the actuating means comprising a composite piezoelectric element having at least one sensor electrode sensing the amplitude of deflection and electronic circuit means operable to energize the piezoelectric element in a pulsed manner, wherein the electronic circuit means includes detection means for comparing the sensed amplitude of deflection with at least one threshold level to provide an indication of abnormal operation of the pump apparatus consistent with occlusion or bubble formation in a volume of the liquid defined by the pump chamber and the inlet and outlet ducts.

An advantage of such apparatus is that abnormal operation of the pump apparatus can be detected instantly and without the need for separate occlusion or bubble sensors.

Preferably the detection means includes occlusion detection means operable to compare the sensed amplitude of deflection against a lower threshold level and indicating the presence of an occlusion when the sensed amplitude is less than the lower threshold level.

Occlusion can thereby be instantly detected and an alarm signal used to generate an audible or visible warning or to turn off the pump automatically.

Preferably the detection means includes bubble detection means operable to compare the sensed amplitude of the deflection against an upper threshold level and indicating the presence of a bubble when the sensed amplitude is more than the upper threshold level.

The presence of a bubble in the pump chamber can thereby be instantly detected since the collapse of an air bubble under pressure will result in over travel of the flexible wall of the pump chamber and hence over travel of the piezoelectric transducer beyond its normal operating range.

Preferably the pump apparatus includes flow rate sensing means connected to the electronic circuit means and the circuit means energizes the piezoelectric transducer at a frequency which is variable to maintain the sensed flow rate at a predetermined level.

Preferably the pump apparatus comprises electrical circuit means operable to control and energise the piezoelectric element whereby the pump apparatus is self-contained and the electrical circuit means is located in a housing which is detachable from the pump body and the housing is connected in use to the pump body by a releasable connecting means.

An advantage of such an arrangement is that the pump body can be made a disposable item whilst the housing can be reusable. Electrical circuitry can therefore be retained within the housing and reused whereas components of the apparatus such as the chamber and valves which make contact with the liquid to be pumped are made disposable. A further advantage is that the pump body can be sterilised prior to use by conventional sterilisation techniques which might not be tolerated by the electrical components within the housing.

Preferably the transducer is located in the housing at a location which overlays the flexible wall of the pump body in use when the housing and pump body are connected in operable relationship and the apparatus includes biassing means biassing the wall into operative engagement with the transducer.

The flexible wall of the pump body then flexes in unison with the transducer so that transducer movement can be sensed and calibrated to provide an accurate measure of the amplitude of each pump actuation.

The biassing means may comprise an annular membrane portion of the flexible wall connected peripherally to a rigid portion of the flexible wall and having a shape memory such that when the pump body is operatively connected to the housing the rigid portion is biassed into engagement with the transducer.

The body may be formed integrally with a reservoir receiving in use a supply of fluid, the reservoir being connected in communication with the inlet duct.

An advantage of such an arrangement is that the pump body and the reservoir containing the supply of fluid can together be supplied as a replaceable item.

The housing may if required include a reservoir compartment receiving the reservoir when the housing and the body are operatively connected and closure means for the reservoir compartment, a priming means being actuated by a manually operated handle mounted on the housing and wherein the handle and the closure means interlock to prevent access to the reservoir compartment when the handle is in a position corresponding to actuation of the priming means to give normal operating condition of the magnetic means.

Preferably each valve comprises a non-return valve having a valve member movable into and out of engagement with a cooperating valve seat in response to pressure or suction generated in the pump chamber by movement of the wall. The apparatus may be provided with magnetic means operable to bias the or at least one of the valve members into a seated position.

Preferably the pump apparatus further comprises priming means selectively operable between a normal operating condition in which the valve biassing means biasses at least one of the valve members into a seated position and a priming condition in which the valve members are biassed by the priming means into an unseated position to allow priming of the pump chamber with fluid.

An advantage of such priming means is that prior to normal pumping operation the valve members can be unseated to allow a free flow of fluid through the pump chamber to fully flush and prime the pump apparatus.

The first and second valve members may each have a respective ferromagnetic portion and the valve biassing means includes first and second annular magnets through which the inlet and outlet ducts respectively extend, the magnets being held in respective valve seats by the priming means in the normal operating condition and being released therefrom in the priming condition for movement to respective further positions in which the valve members are no longer biassed into a seated position.

An advantage of this arrangement is that the valve members can be unseated without any danger of introducing air or other contaminant to the flow path defined by the pump chamber and the inlet and outlet ducts, the magnetic means being located externally with respect to the parts of the pump body defining the flow path.

According to a further aspect of the present invention there is disclosed a pump apparatus comprising a pump body defining a pump chamber, a displaceable wall of the pump body being displaceable to vary the volume of the pump chamber, biassing means biassing the displaceable wall into a fully extended position in which the volume of the chamber is maximised, a housing, connecting means releasably connecting the housing to the pump body the housing comprising a piezoelectric transducer operable to reciprocatingly move the displaceable wall when the housing and the pump body are connected, wherein the connecting means comprises cam means operable between the pump body and the housing during connection of the pump body to the housing to move the pump body from a first position relative to the housing in which the displaceable wall is in its fully extended position in abutment with the transducer and a second position relative to the housing in which the displaceable wall is partially extended in its normal operating position whereby the displaceable wall is biassed into contact with the transducer by action of the biassing means such that contact is maintained during reciprocation of the transducer.

An advantage of such pump apparatus is that during connection of the pump body to the housing the displaceable wall is depressed from its fully extended position to its partially extended position in a controlled manner through a displacement which can be accurately controlled to a predetermined value. It is particularly important where the biassing force exerted on the displaceable wall is proportional to the displacement of the displaceable wall from its fully extended position so that any error in the displacement relative to the preferred predetermined value will result in the biassing force being either too great or too little for the provision of effective pumping action.

Preferably the connecting means comprises at least one locking member connected to the housing and movable between an unlocked position and a locking position in which a foot portion of the locking member overlays a contact surface of the pump body so as to prevent disconnection of the pump body from the housing.

Conveniently at least one of the foot portion and the contact surface comprises a ramped surface such that movement of the locking member into the locking position provides cam action whereby the foot portion and the contact surface together constitute the cam means.

Preferably the pump apparatus comprises a plurality of locking members which are peripherally spaced relative to the displaceable wall, the locking members being mounted on a mounting member so as to be movable in unison between their respective locking and unlocked positions.

An advantage of this arrangement is that the peripheral spacing of the locking members ensures that an evenly distributed load is applied to the pump body both during the locking movement and during the continued connection of the housing to the pump body to thereby avoid possible distortion and imperfect connection to the housing.

Conveniently the housing member comprises an annular flange and the housing further comprising annular guide means cooperating with the flange to facilitate axial rotation of the annular flange between positions corresponding to the unlocked and locking positions of the locking members.

Preferably the pump body is provided with at least one aperture through which a cooperating locking member extends when the housing is connected to the pump body.

Such an arrangement assists in indicating to the user the correct positioning of the body relative to the housing during connection and assists in achieving alignment between the displaceable wall and the transducer.

Preferably the displaceable wall is formed of an elastomeric material and includes a relatively thick central portion which is relatively rigid and a relatively flexible annular membrane portion connected peripherally to the rigid portion, the membrane portion having a shape memory such that the central portion is biassed into the fully extended position to thereby constitute the biassing means.

Preferably the transducer of the above described pump apparatus comprises a wafer of piezoelectrically active material, a drive electrode bonded to a first major face of the wafer, a ground electrode bonded to a second major face of the wafer, the drive electrode being provided with a cut-out revealing an elongate exposed portion of the wafer, a sense electrode bonded to the exposed portion and a screening electrode bonded to the exposed portion at a location intermediate the sense electrode and the drive electrode, the screening electrode being electrically connected to the ground electrode in use to provide electromagnetic screening of the sense electrode from a drive voltage applied to the drive electrode, whereby the sense electrode is operable to produce a signal representative of deflection of the wafer.

The output signal produced by the sense electrode in response to deflection of the wafer is thereby substantially free of interference resulting from the drive voltage present on the adjacent drive electrode.

DESCRIPTION OF PREFERRED EMBODIMENTS

Preferred embodiments of the present invention will now be described by way of example only and with reference to the accompanying drawings of which:

FIG. 8 is a plan view of a further alternative pump apparatus having a key pad and display;

FIG. 9 is an elevation of a further alternative pump apparatus connected to a supply pack and flexible tube;

FIG. 10 is an elevation of the apparatus of FIG. 9 showing a housing of the apparatus being presented to a disposable body of the apparatus prior to an infusion;

FIG. 21 is a side elevation of a transducer of the apparatus of FIGS. 16 to 20; and FIG. 22 is a plan view of the transducer of FIG. 21.

Figure 1:
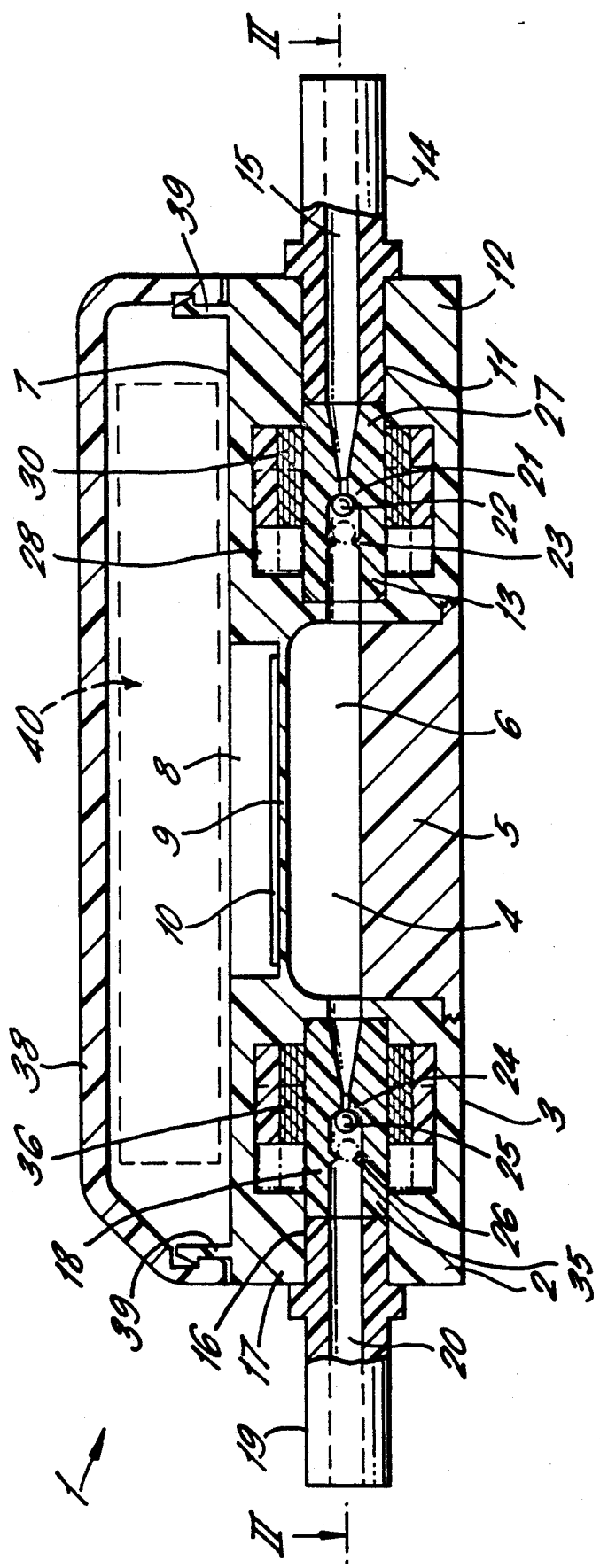
FIG. 1 is a side elevation of pump apparatus in accordance with the present invention.

FIG. 1 shows apparatus 1 for use in the delivery of a drug intravenously to a patient. Apparatus 1 comprises an elongate body 2 moulded from a plastics material. The body 2 is of rectangular cross-section and has a bottom surface 3 in which is formed a cylindrical recess 4. A screw-threaded plug 5 fits sealingly into the recess 4 to define a chamber 6 within the recess. The plug 5 is moulded from polystyrene containing 40% glass fibres.

The body 2 has a top surface 7 in which is formed a second cylindrical recess 8 such that a thin membrane 9 is defined between the first and second recesses 4 and 8 and forms a flexible wall to the chamber 6.

A piezoelectric membrane 10 overlays the flexible membrane 9, the respective membranes 9 and 10 being in intimate contact such that any flexure of the piezoelectric membrane is accompanied by conformal flexure of the flexible membrane.

A first longitudinal bore 11 is formed in a first end 12 of the body 2 and receives a first non-return valve 13 and a first cylindrical connector 14 defining an inlet duct 15 communicating with the chamber 6.

A second bore 16 is formed longitudinally in the second end 17 of the body 2 and receives a second non-return valve 18 and a second tubular connector 19 defining an outlet duct 20 communicating with the chamber 6.

The first non-return valve 13 comprises an annular valve seat 21 through which the inlet duct 15 extends and includes a spherical steel valve member 22 coated in polytetrafluorethylene (PTFE). The valve member 22 is movable longitudinally within the inlet duct to an extent limited in a direction away from the seat 21 by projections 23 which project radially inwardly of the duct.

The second non-return valve 18 is similarly provided with a valve seat 24, a spherical valve member 25 and projections 26. The first and second non-return valves 13 and 18 are arranged such that in each case flow of fluid in a direction from the outlet duct to the inlet duct is prevented by sealing engagement of the respective valve member 21, 25 with the respective seat 21, 24.

Figure 2:
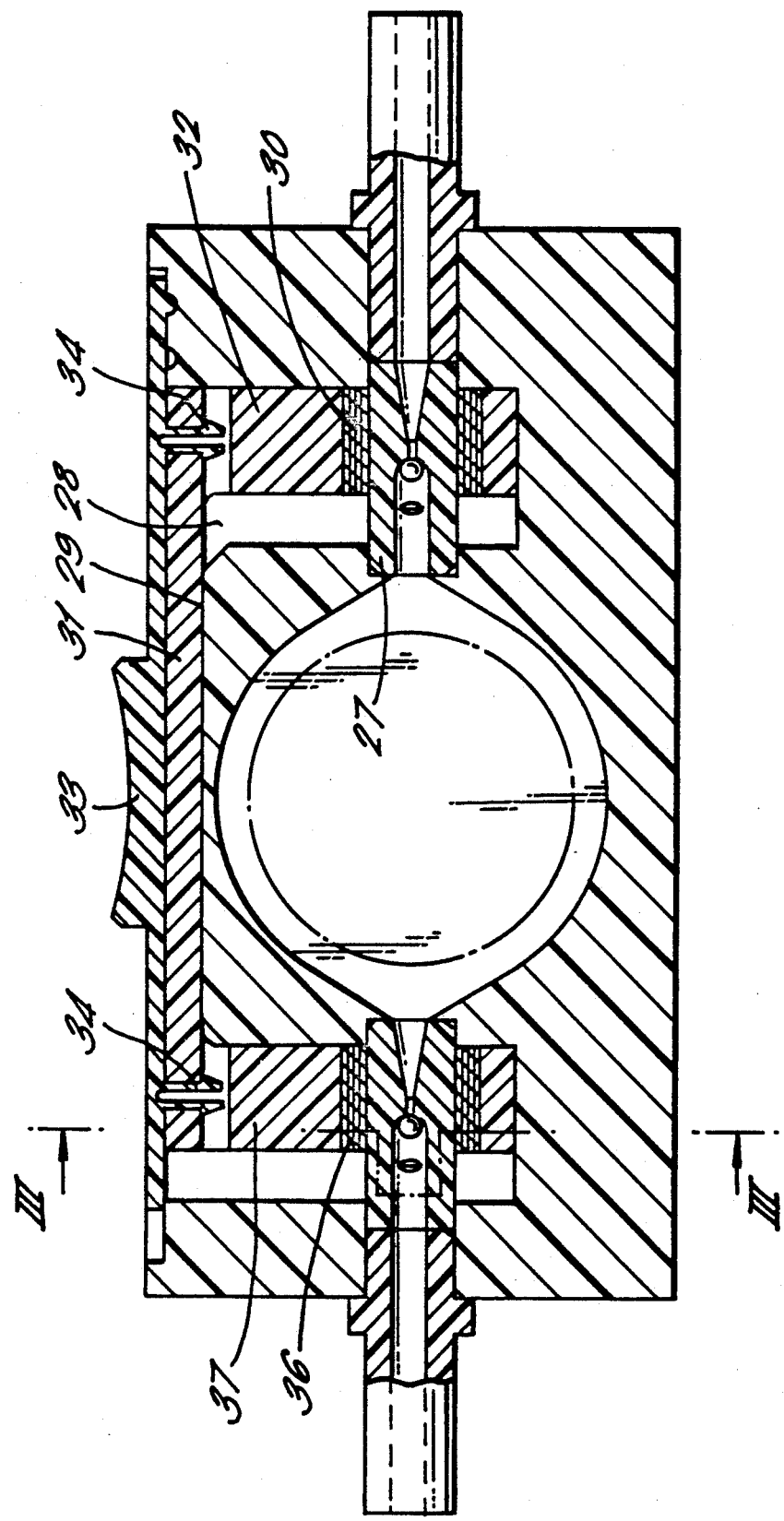
FIG. 2 is a sectioned plan view of the apparatus of FIG. 1.

The first non-return valve 13 has a cylindrical valve body 27 which intersects a first aperture 28 which extends transversely into the body 2 from a right-hand side surface 29 of the body 2 as seen in FIG. 2. A first annular magnet 30 is coaxially mounted on the first valve body 27 and is axially slidable relative to the valve body between the normal position as shown in FIG. 1 and a pump priming position shown in broken lines. In its normal position the centre of magnet 30 lies between the seat 21 and the first end 12 of the body 2. In its priming position the centre of magnet 30 lies on the other side of the seat 21 adjacent the projections 23. A slider plate 31 is mounted in contact with the right-hand side surface 29 so as to be longitudinally slidable relative to the body 2 and is connected to the first annular magnet 30 by a first arm 32. A handle 33 is connected to the slider plate 31 by means of snap fit connectors 34.

The second non-return valve 18 similarly has a cylindrical valve body 35 on which a second annular magnet 36 is axially slidable, the second magnet being connected to the slider plate 31 by a second arm 37. The first and second magnets 30 and 36 are thereby movable between respective normal and priming positions by actuation of handle 33.

A housing 38 is detachably connected to the body 2 by means of snap fit connectors 39 so as to overlay the top surface 7. The housing 38 contains a control unit 40 represented schematically by broken lines as occupying the housing.

The control unit 40 includes releasable connecting means (not shown) operable to make electrical connection with the piezoelectric membrane 10. The control unit 40 contains a battery (not shown) and programmable circuitry for energising the piezoelectric membrane 10 so that the apparatus 1 is self-contained.

In use the first connector 14 is connected to a supply of fluid and the slider plate 31 is manually moved into a pump priming position (to the left in FIG. 1). In this position the valve members 22 and 25 are unseated from the respective valve seats 21 and 24 by magnets 30 and 36 respectively. Fluid is then able to flow through the inlet duct 15, the chamber 6 and the outlet duct 20 so as to prime the apparatus 1.

The slider plate 31 is returned to its normal position (to the right in FIG. 1) in which the valve members 22 and 25 are held in contact with respective valve seats 21 and 24 by magnets 30 and 36 respectively thereby preventing flow of fluid through the apparatus.

To commence an infusion the second connector 19 is connected to a suitable fluid filled cannula in a manner which avoids introduction of air into the cannula or the apparatus 1.

Infusion is commenced by turning on the control unit 40 which is programmed to deliver actuating electrical pulse sequences to the piezoelectric membrane 10. Each actuating pulse sequence consists of a positive pulse followed by a negative pulse of the same amplitude and duration and the frequency with which pulse sequences are generated is varied by the control unit 40 in accordance with the required flow rate.

At each positive actuating pulse the piezoelectric membrane 10 flexes in a direction towards the flexible membrane 9 thereby causing corresponding flexure of the membrane 9 which results in a decrease of the volume of chamber 6. Fluid in chamber 6 is thereby pressurised and the second non-return valve 18 is opened under fluid pressure, the valve member 25 being unseated from its valve seat 24 and held against projection 26 in a position which allows fluid flow from the chamber 6 through the outlet duct 20.

At the end of the positive actuating pulse the membrane 10 relaxes to its initial position as shown in FIG. 1 as does the flexible membrane 9 thereby restoring the chamber 6 to its original volume and creating suction within the chamber 6. The second non-return valve 18 is closed by this suction as the second valve member 25 seats against the valve seat 24 and simultaneously the first non-return valve 13 is opened as the valve member 22 is unseated from its valve seat 21 and is held against projections 23 in a position which allows flow of fluid to pass from the inlet duct into the chamber 6.

A negative actuating pulse is then received by the piezoelectric membrane 10 which flexes in a direction away from the flexible membrane 9 thereby causing corresponding flexure of the membrane 9 which results in an increase in the volume of chamber 6. Suction is then created within chamber 6 which draws fluid into the chamber through the first non-return valve 13. At the end of the negative actuating pulse the membrane 10 relaxes to its initial position as shown in FIG. 1 as does the flexible membrane 9 thereby restoring the chamber 6 to its original volume and creating pressure within the chamber. This pressure results in a first non-return valve 13 being closed and the second non-return valve 18 being opened accompanied by fluid being pumped under pressure from the chamber to the second non-return valve and out through the outlet duct 20. During the interval between successive actuating pulse sequences the first and second non-return valves 13 and 18 are closed by action of the first and second magnets 30 and 36 which maintain a constant bias of the valve members 21 and 25 towards their respective valve seats 21 and 24.

At each cycle of operation of the apparatus 1 as described above a substantially constant volume of liquid is pumped so that the flow rate at which an infusion proceeds is determined by the frequency of actuating pulses controlled by the control unit 40.

Figure 3:
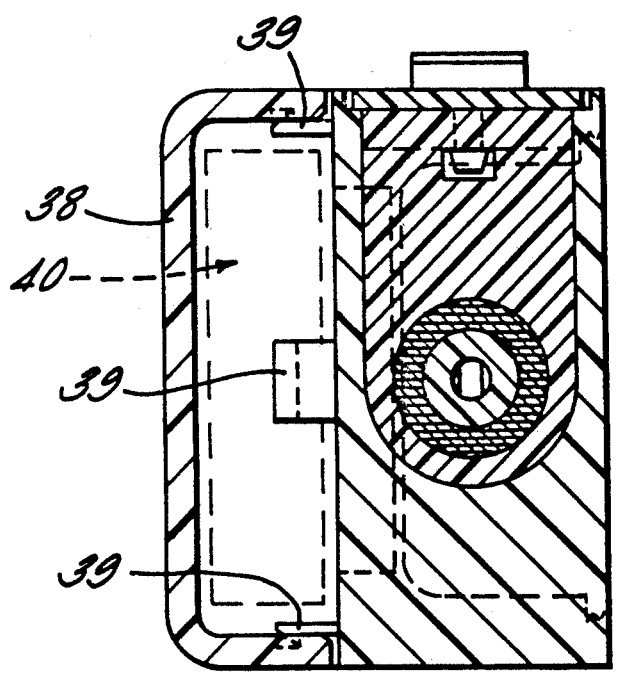
FIG. 3 is a sectioned end elevation of the apparatus of FIGS. 1.

A modification to the apparatus 1 will now be described with reference to FIG. 4 and using reference numerals corresponding to those of FIGS. 1 to 3 for corresponding elements where appropriate.

Figure 4:
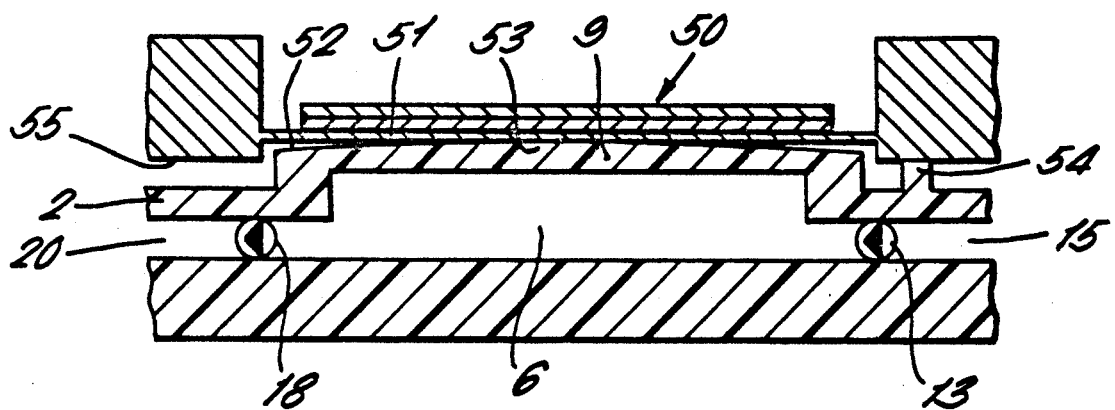
FIG. 4 is a sectional elevation of part of an alternative apparatus showing detail of the piezoelectric transducer.

In FIG. 4 a composite piezoelectric membrane 50 is located in the housing 38 and is attached to a thin flexible membrane 51 forming an external surface of the housing.

The housing 38 is detachably connected to a body 2 connected to an inlet duct 15 and an outlet duct 20 via first and second non-return valves 13 and 18 respectively (represented schematically in FIG. 4).

The body 2 includes a flexible membrane 9 forming a flexible wall to the chamber 6 and the body membrane 9 has a domed external surface 52 having an apex 53 which maintains contact with the planar housing membrane 51.

Three locating lugs 54 project from the body 2 in circumferentially spaced positions relative to the flexible body membrane 9 and abut with an annular surface 55 of the housing 38 which is connected to the housing membrane 51 such that the housing membrane 51 is peripherally supported at a fixed distance relative to the body 2.

Figure 5:
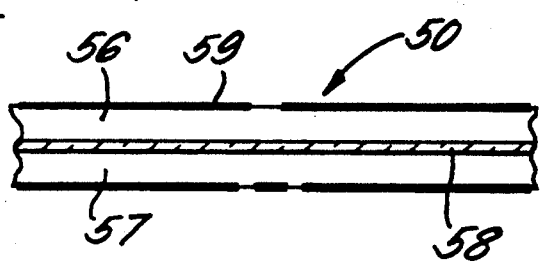
FIG. 5 is an enlarged view of the transducer of FIG. 4.

The structure of the composite piezoelectric membrane 50 is shown in FIG. 5 in enlarged scale. The composite piezoelectric membrane 50 comprises upper and lower ceramic discs 56 and 57 respectively separated by a brass disc 58. Upper and lower metallic drive electrodes 59 and 60 respectively are formed on the upper and lower surfaces of the upper and lower discs 56 and 57 respectively and are electrically connected to the control unit 40 so as to receive actuating pulses resulting in flexure of the membrane 50 by electrical polarisation of the ceramic discs 56 and 57.

Figure 6:
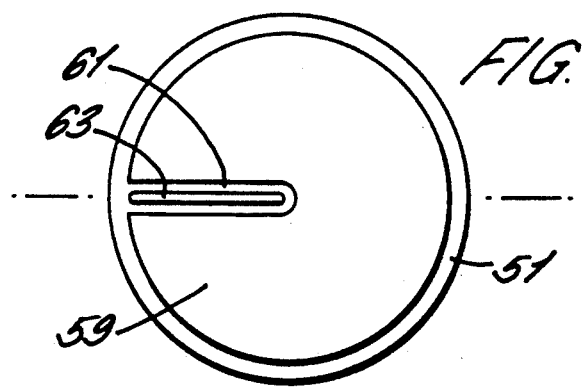
FIG. 6 is a plan view of the transducer of FIGS. 4 and 5.
Figure 7:
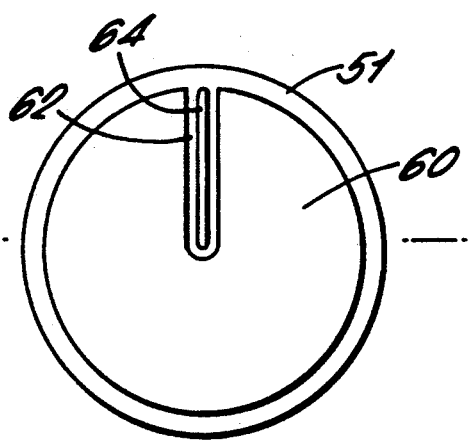
FIG. 7 is an underneath view of the transducer of FIGS. 4 to 6.

The upper and lower drive electrodes 59 and 60 each include radially extending cutouts 61 and 62 respectively which are angularly spaced by 90° as seen from FIGS. 6 and 7 and upper and lower sense electrodes 63 and 64 respectively extend radially within the respective cutouts 61 and 62 so as to be electrically isolated from the drive electrodes.

The upper and lower sense electrodes 63 and 64 are connected to the control unit 40 to provide feedback as to the extent of flexure of the piezoelectric membrane 50 and hence feedback as to the corresponding flexure of the body membrane 9. The control unit 40 is provided with circuitry (not shown) deriving a signal representing the amplitude of flexure of the membranes 50 and 9 and comparing the signal with maximum and minimum threshold levels to generate alarm signals if the signal is not within these upper and lower limits. In this way the apparatus 1 is able to indicate fault conditions arising either from the presence of air bubbles in the pump chamber 6 or occlusion of the downstream infusion path with respect to the pump chamber.

The effect of an air bubble being formed within the pump chamber 6 is that flexure of the membrane 9 so as to reduce the volume of the pump chamber would result in reduction in the volume of the air bubble since air is readily compressible whereas the surrounding liquid is highly incompressible. Consequently the extent of travel through which the membrane 9 flexes will be greater than during a normal pump actuation in the absence of any air bubble and consequently the signal amplitude derived from the sense electrodes 63 and 64 will be greater than usual and can be detected as such by comparison with a predetermined upper threshold level.

Similarly the effect of an occlusion downstream of the pump chamber 6 for example in the outlet duct 20 would be that liquid would be prevented from leaving the chamber 6 on being compressed by flexure of the membrane 9 and the incompressibility of the liquid would limit flexure of membrane 9 to less than during a normal pump actuation. The amplitude of the signal derived from the sense electrodes 63 and 64 would therefore be less than usual and can be detected as such by comparison with a predetermined lower threshold level.

During normal operation the output signal derived from the sense electrodes 63 and 64 provides a measure of the volume of liquid metered at each actuation of the apparatus 1. The control unit 40 is programmed to deliver a predetermined flow rate and adjusts the actuating pulse frequency to achieve the required flow rate according to the signal amplitude. In the above examples the range of actuating pulse frequency during normal operation is between 25 and 50 Hz and the swept volume of the pump chamber is one microliter.

The housing 38 may be of any convenient external shape providing that it is adapted to mate with the body 2 and may for example include a keypad 70 and display 71 as shown in FIG. 8. The keypad 70 has a PUMP button 72, a CONFIRM button 73, a STEP UP button 74 and STEP DOWN button 75 for the input of data to the control unit 40.

The display 71 is of a liquid crystal type and further includes light emitting diode indicators 76 to 84. An electro acoustic transducer 85 capable of generating an audible warning is also mounted on the housing 38.

A keyhole 86 for receiving an actuating key is also provided in the housing 38.

In use a user primes the apparatus 1 before connection of the body 2 to the housing 38 as described above. The housing 38 is then clipped to the body 2 after which the control unit 40 automatically carries out some self-checking steps to establish whether good contact has been made with the body 2, whether the battery voltage is adequate, that the display and audible warning 85 are in order, that there is no air in the chamber 6 and that there is no occlusion in the apparatus 1 (these latter checks requiring some initial actuations of the piezoelectric membrane 10).

The self-check as to the correct operation of the display 71 and audible transducer 85 is carried out by the control unit illuminating all of the indicators 76 to 84 and sounding the transducer 85 at which the user should respond by pressing the CONFIRM button 73. On receiving this confirmation the control unit 40 ceases to illuminate the indicators 76 to 84 and turns off the transducer 85. Indicator 76 which is designated as PROGRAMME indicator is then made to flash on and off to indicate to the user that the control unit 40 is ready to receive programming instructions. The user then inserts a key into the keyhole 86 to actuate a key switch (not shown) permitting entry of programme data. At this point the indicator 82 which is designated as VOLUME IN MILLILITERS is illuminated and the user enters the required data for the volume of infusion by scrolling the numerical display 71 using the STEP UP or STEP DOWN key 74, 75 as required. When the required number is indicated by the display 71 the data is entered by pressing the CONFIRM button 73.

A similar procedure is then followed to enter further data prompted by illumination of indicator 83 designated as RATE in milliliters per hour, indicator 81 designated as BOLUS and indicator 84 which is designated as TIME INTERVAL.

The user can therefore programme the duration and rate of an infusion together with the maximum volume required. The bolus setting indicates a preset bolus volume which can be delivered if the need should arise during the infusion i.e. if a higher flow rate is required for a short duration as in the case of the need to administer a pain killer at an increased dosage.

On completion of programming the key is removed and the PUMP button 72 pressed to commence the infusion. Removal of the key prevents a patient from changing any of the programmed settings. An audible warning is generated by the transducer 85 five minutes before completion of the infusion in order to alert an operator that completion is imminent. Completion of the delivery of the required volume is displayed by the control unit 40 turning off the indicator 79 denoted as a PUMPING indicator and an audible warning is sounded by the transducer 85.

Indicator 77 is designated AIR BUBBLES and will be lit if an air bubble is detected. An audible warning is also produced using transducer 85. Similarly illumination indicator 78 corresponds to detection of occlusion. The alarm signal generated by the transducer 85 can be silenced by an operator pressing the CONFIRM button 73.

Indicator 76 is designated as a LOW BATTERY indicator.

On completion of the infusion the housing 38 is unclipped from the body 2 and the body 2 is disposed of as waste. An important advantage of the pump apparatus of the present invention when used in medical applications is that whereas the electronic control apparatus within the housing 38 is reusable the body 2 is disposable and of relatively low cost so that the body can be repeatedly and frequently renewed. This is important because of the micro biological hazards of infusion therapy and the need to comply with administration procedures requiring infusion apparatus to be changed at regular intervals.

The control unit 40 is also provided with a separate rechargeable battery which is connected so as to maintain programme memory during periods in which the control unit is not connected to its normal power supply battery. The control unit may then be programmed to maintain a log of each use of the apparatus over an extended period of time. The control unit may also be programmed to display on demand an indication of the total time for which a particular disposable pump body 2 has been in use.

In FIGS. 9 and 10 apparatus 90 of alternative external shape is illustrated, corresponding reference numerals to those of apparatus 1 being used where appropriate.

In FIG. 9 a housing 38 is being presented to a disposable body 2 prior to an infusion.

In FIG. 10 the housing 38 is shown connected to the body 2 during an infusion in which a supply pack 91 is connected to the first connector 14. The second connector 19 is connected to a cannula (not shown) via a flexible tube 92 to which is fitted a shut off valve 93 and a luer connector 94.

The apparatus is powered by a battery which may be located either within the housing or within the pump body. If it is located within the pump body then this has the advantage that if the pump body is a disposable item then a new battery is provided with each successive use with a given housing.

The materials used in the pump body must be selected to be compatible with the liquid to be pumped. This is particularly true of medical applications where medically approved plastics materials are essential.

The apparatus may additionally be provided with means which allow operative connection of the housing only to approved pump bodies so as to exclude for example pump bodies copied by competitors and possibly of an inferior quality. These means may for example include a surface relief holographic element on the pump body which is scanned by a light detector in the housing. Simple mechanical interlocks may also be provided.

The apparatus may be modified to include a further bubble detector of known type such as a sensor responsive to optical refraction of the contents of the inlet duct. This provides an additional safeguard against bubbles entering the apparatus and can be used to generate warnings in the same manner as the bubble detection circuit incorporated in the control unit 40 and responsive to flexure of the piezoelectric membrane.

Figure 11:
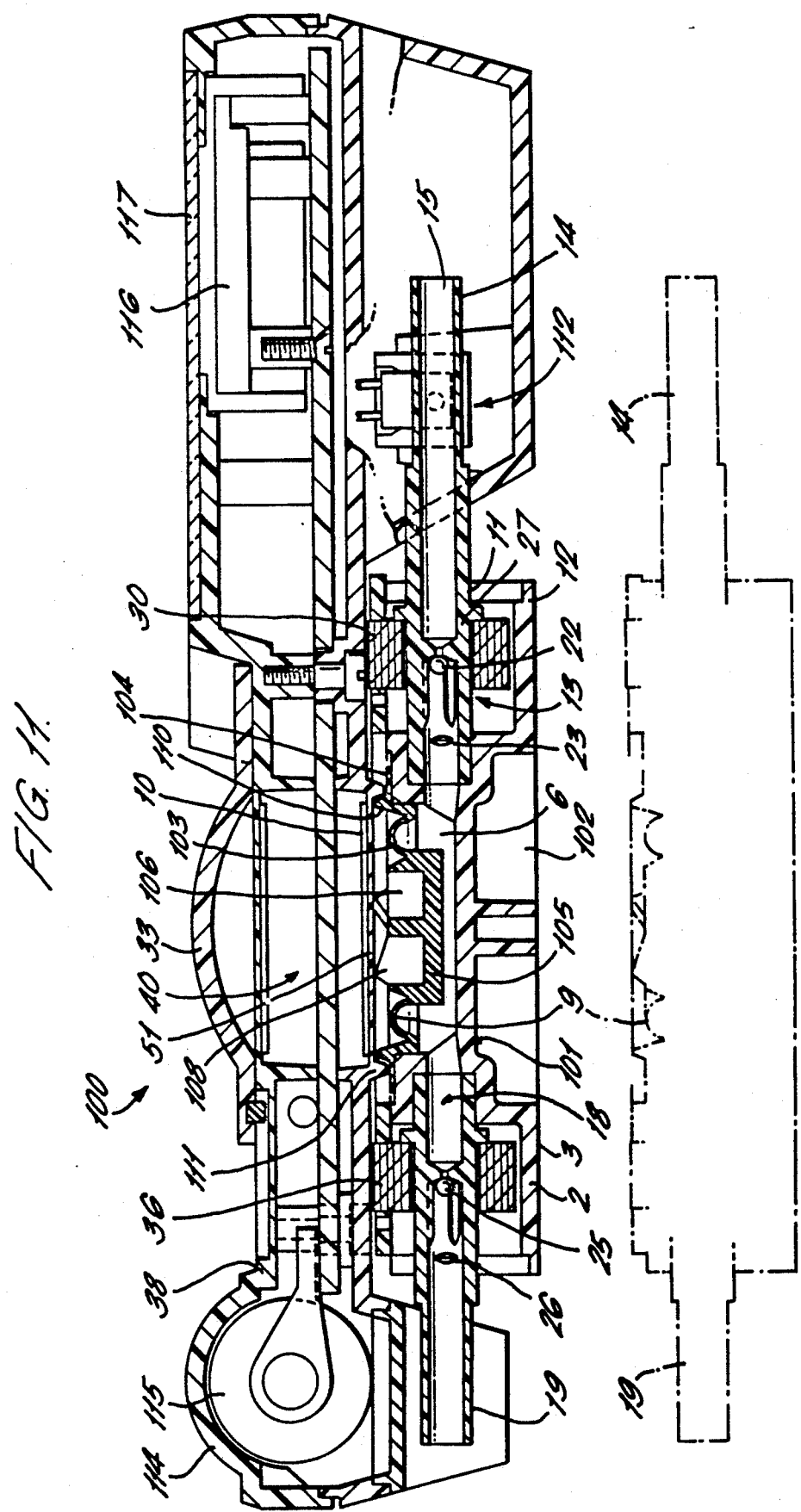
FIG. 11 is a sectional elevation of a further alternative pump apparatus.
Figure 12:
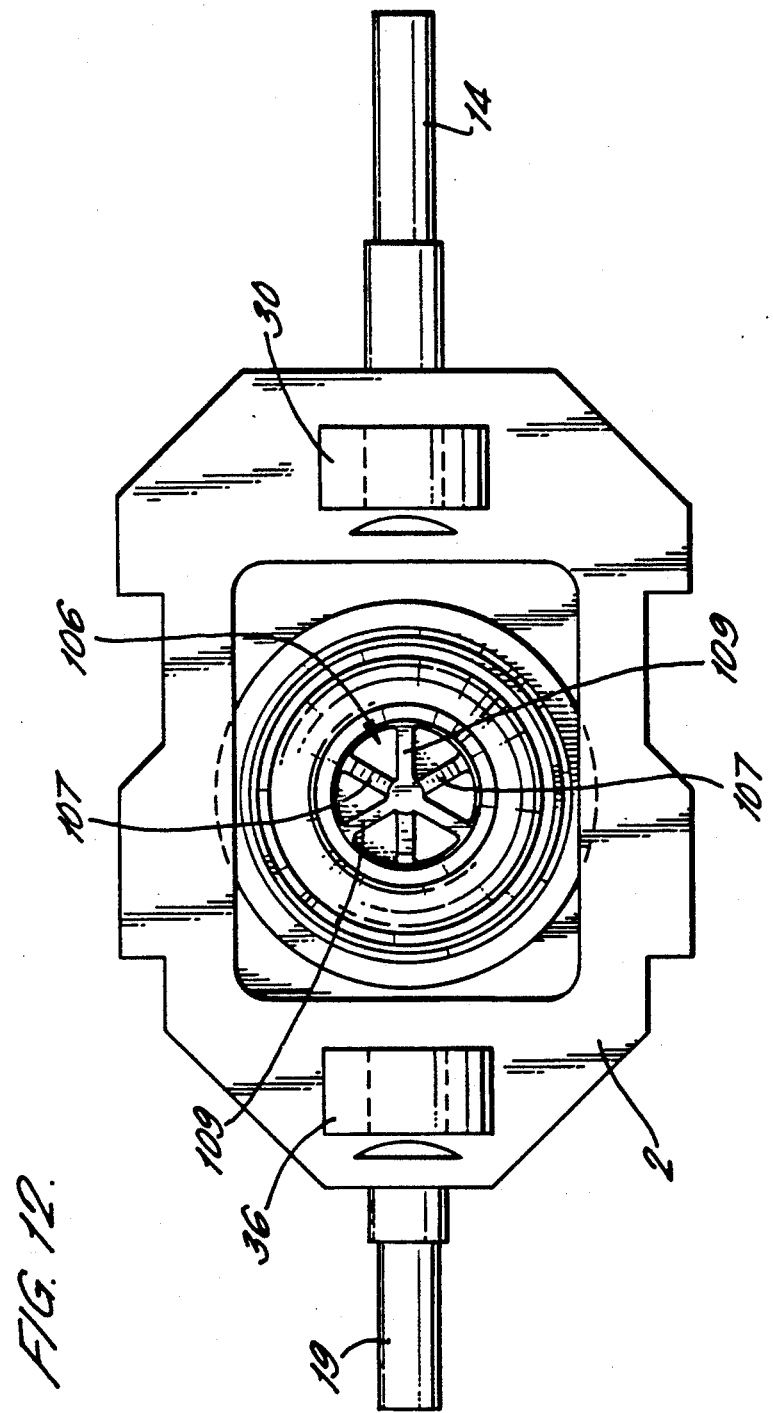
FIG. 12 is a plan view of the pump apparatus of FIG. 11.
Figure 13:
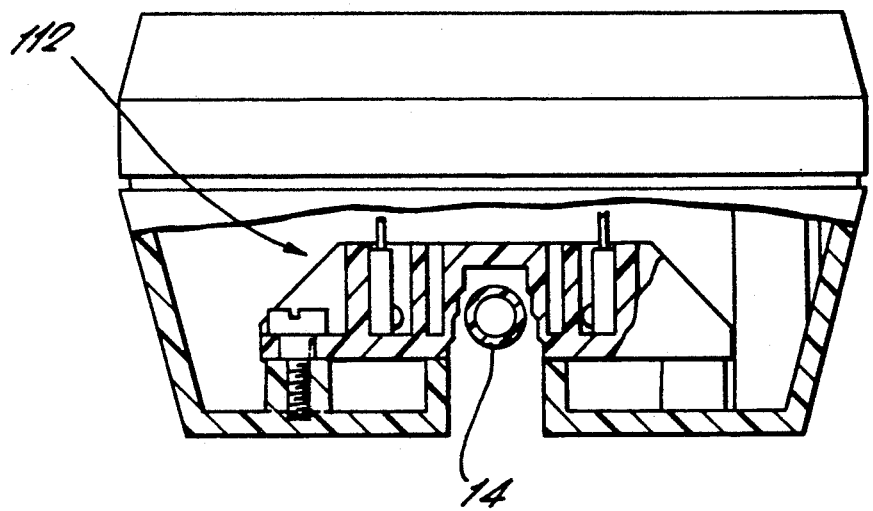
FIG. 13 is an end view partially in section of the apparatus of FIGS. 11 and 12.

FIGS. 11, 12 and 13 show a further alternative apparatus 100 which includes many features in common with the apparatus described with reference to the previous Figures and therefore corresponding reference numerals for corresponding elements are used where appropriate. Apparatus 100 has a body 2 formed of a transparent medically approved plastics material. The body 2 is intended to be a disposable item and is shown in the upper portion of FIG. 11 connected to a non-disposable housing 38 and is also shown in outline in the lower portion of FIG. 11 in which it is separated from the housing.

The body 2 has a bottom surface 3 having a circular central portion 101 which is strengthened by radially extending stiffening ribs 102. Above the central portion 101 a chamber 6 is defined within the body 2 and the volume of the chamber is variable by flexure of a flexible membrane 9 forming a flexible wall to the chamber 6. The flexible membrane 9 comprises an annular flexible portion 103 of semi-circular cross-section connected between an outer support ring 104 and a central rigid disc 105. A spider member 106 is formed integrally with the disc 105 such that the spider member and disc together form a rigid assembly which is movable vertically relative to the support ring 104 by flexure of the flexible annular portion 103.

As seen more clearly in FIG. 12 the spider member 106 includes three radially extending arms 107 each including a vertically extending projection 108 of triangular elevation. Between the arms 107 three further arms 109 are also provided, these further arms being similar to arms 107 but not being provided with features corresponding to the projections 108.

The support ring 104 is bonded to the body 2 to thereby seal the chamber 6 and the support ring also includes an externally projecting annular raised lip 110.

The housing 38 is connectable to the body 2 such that an annular flange 111 locates around the lip 110. The housing includes a membrane 51 within the annular flange 111 which in the connected configuration as shown in FIG. 11 is positively held in contact with the projections 108 of the spider member 106. A piezoelectric membrane 10 overlays the housing membrane 51 such that the membrane 51 is flexible in unison with the piezoelectric membrane.

The annular flexible portion 103 has a shape memory such that whenever body 2 is operatively connected to the housing 38 the spider member 106 is biassed into contact with the housing membrane 51 with a force equivalent to a weight of 500 grammes. The disc 105 therefore moves in unison with the piezoelectric membrane 10.

The body 2 is provided with first and second tubular connectors 14 and 19 respectively which communicate with the chamber 6 via first and second valves 13 and 18 respectively of similar type to those of the apparatus 1. The apparatus 100 further includes an air bubble detector 112 which is connected to the housing 38 such that when the body 2 is connected to the housing the first tubular connector extends through the bubble detector. The bubble detector 112 is of known type comprising a light source on one side of the tubular connector 14 and a light sensor on the opposite side of the connector and sensitive to change in the refractive index of the contents of the duct 15 defined by the tubular connector. The detector 112 supplements the means of bubble detection referred to above with reference to apparatus 1.

Housing 38 includes a control unit 40 mounted on a printed circuit board 113 and further includes a battery compartment 114 containing a replaceable battery 115. The control unit 40 is also connected to an auxiliary battery (not shown) which maintains the memory functions of the control unit during replacement of the replaceable battery 115.

The housing 38 further includes a liquid crystal display 116 which is viewable through a transparent window 117.

The housing 38 includes a handle 33 which is connected to first and second annular magnets 30 and 36 respectively and arranged so as to be slidable longitudinally of the housing between a normal position as shown in FIG. 11 and a priming position (not shown) in which the magnets are moved to the left of FIG. 11 so as to unseat valve members 22 and 25 during a priming operation.

Figure 14:
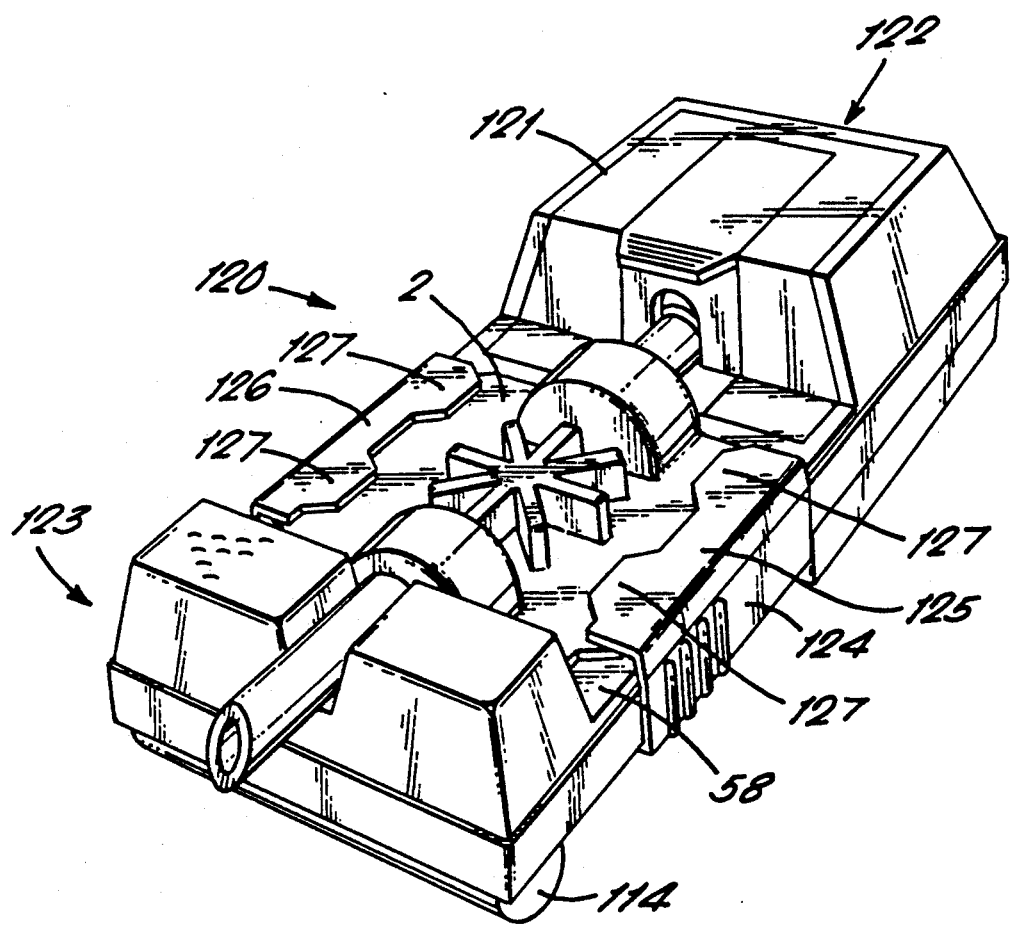
FIG. 14 is a perspective view of an alternative pump apparatus having an integral reservoir.
Figure 15:
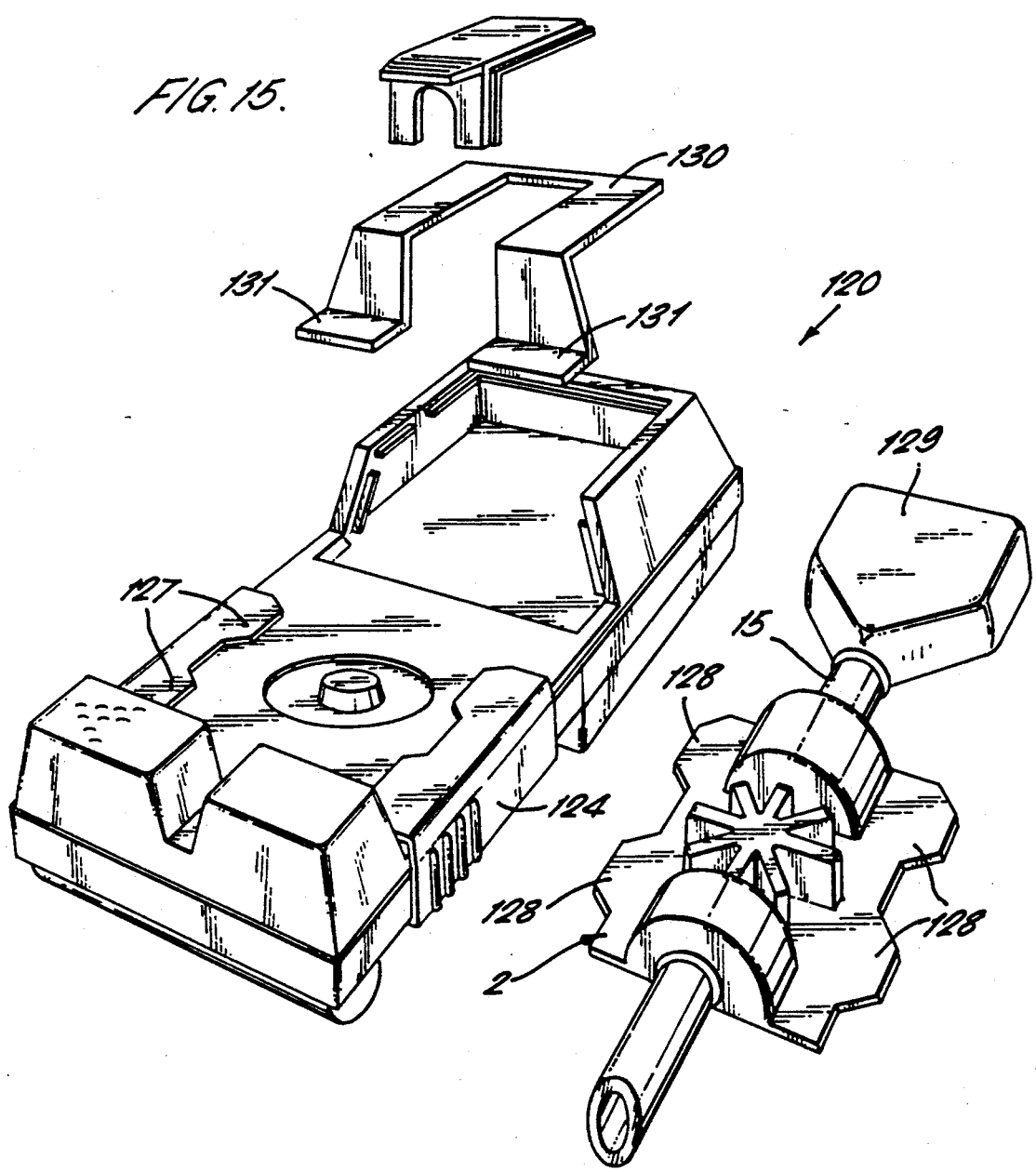
FIG. 15 is a perspective exploded view of the apparatus of FIG. 14.

A further alternative apparatus is shown in FIGS. 14 and 15 where corresponding reference numerals to those of previous Figures are used where appropriate for corresponding elements.

The apparatus 120 has a housing 58 with a reservoir compartment 121 at a first end 122 of the housing. A battery compartment 114 is located at a second end 123 of the housing.

A sliding handle 124 is longitudinally slidably mounted on the housing 58, the handle being generally of U-shaped cross-section with inturned edge portions 125 and 126 each having projecting tabs 127 which overlay and thereby hold in place the disposable body 2. The apparatus 120 of FIGS. 14 and 15 is shown in a different orientation to the apparatus of previous Figures i.e. such that the body 2 is uppermost.

As seen in FIG. 15 the body 2 includes laterally projecting lugs 128, the respective lugs 127 and 128 being longitudinally spaced so as to be inter-digitated during connection of the body 2 and the housing 58. A reservoir 129 comprising a collapsible plastic sac is connected to the inlet duct 15. When the disposable body 2 is connected to the housing 58 the reservoir 129 is concealed within the reservoir compartment 121 which is accessible via a laterally slidable reservoir cover 130. The reservoir cover 130 includes laterally projecting lugs 131 which in the normal operating position of the handle 124 are overlaid by lugs 127 such that the reservoir cover cannot be removed.

In order to load a fresh disposable body 2 into the housing 58 the handle 124 must first be moved fully towards the second end 123 of the housing and the reservoir cover 130 removed. The disposable body and reservoir 129 can then be loaded on to the housing 58 and the reservoir cover 130 replaced. The handle 124 is then moved fully towards the first end 122 of the housing 58 such that the lugs 127 overlay the lugs 128 of the disposable body 2 and also overlay the lugs 131 of the reservoir cover. Both the body 2 and the reservoir cover 130 are then held in position.

During this procedure the initial position of the handle 124 is such that the magnets 30 and 36 are in their priming position (as described with reference to FIG. 1). After movement of the handle towards the first end 122 the magnets 30 and 36 are moved to their normal operating position in which the first and second non-return valves 13 and 18 open and close in response to fluid pressure.

In an alternative embodiment the spherical valve members may be replaced by a bullet-shaped valve member.

The non-return valves may alternatively be moved to their priming positions by an electromagnet.

The reservoir may carry an identifying coded element which can be read by a suitable detector of the housing such that the control unit 40 is automatically provided with data when a fresh body 2 complete with drug reservoir 129 is loaded to the housing. The control unit 40 may be programmed on receipt of this data to deliver the drug in accordance with predetermined parameters without the need for operator input. The control unit 40 may also record and display the total dose of drug delivered from a given reservoir and generate an alarm when the supply is nearly exhausted.

Figure 16:
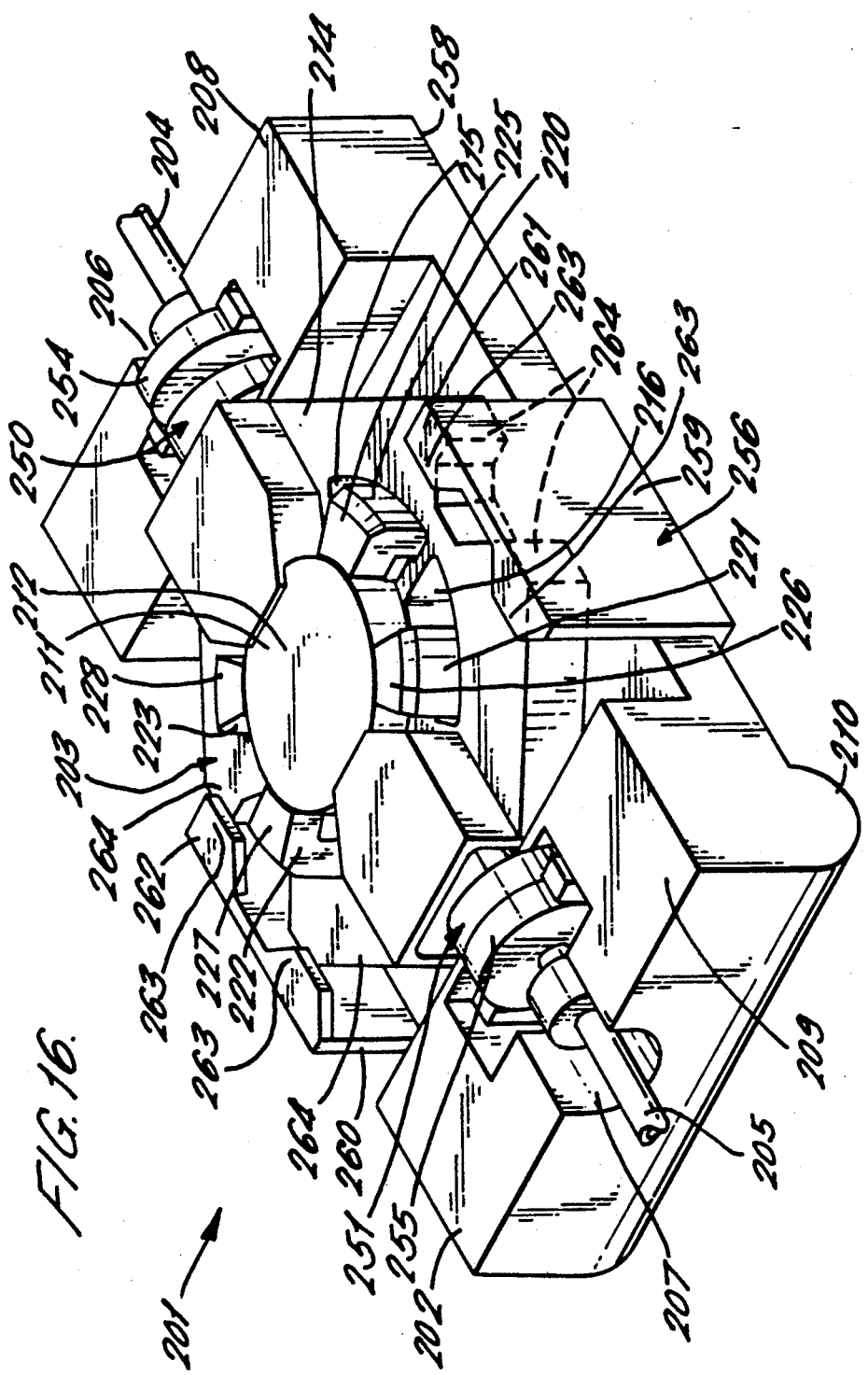
FIG. 16 is a perspective view of a further alternative pump apparatus having a pump body operatively connected to a housing.

In FIG. 16 a further alternative pump apparatus 201 has a housing 202 which is operatively connected to a pump body 203.

The pump body 203 has an inlet duct 204 and an outlet duct 205 which are received in first and second recesses 206 and 207 provided in first and second end portions 208 and 209 of the housing 202 respectively. The second end portion 209 includes a battery compartment 210 for powering electronic circuitry (not shown) contained within the housing 202.

Figure 18:
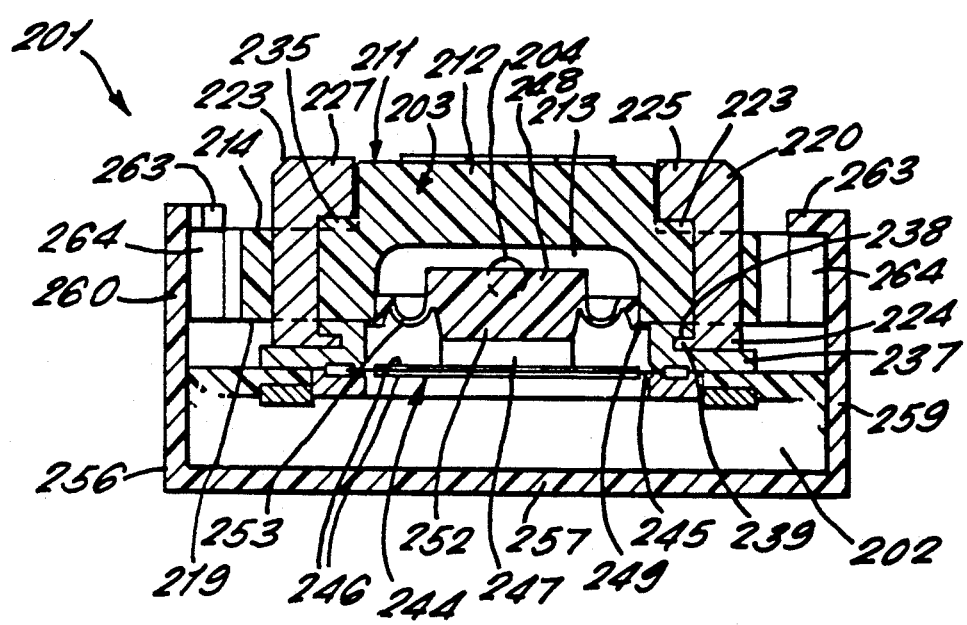
FIG. 18 is a section taken at XVIII of the pump apparatus of FIGS. 16 and 17.

The pump body 203 includes a centrally located cylindrical portion 211 projecting at right angles to the inlet and outlet ducts 204 and 205 and constituting a rigid wall 212 of a chamber 213 as shown in FIG. 18.

The cylindrical portion 211 projects from a planar upper surface 214 of the pump body 203 and first, second, third and fourth part-annular apertures 215, 216, 217 and 218 are circumferentially spaced peripherally of the cylindrical portion 211 so as to communicate between the upper surface 214 and a lower surface 219 of the pump body.

First, second, third and fourth locking members 220, 221, 222 and 223 project upwardly from an annular mounting member 224 to which they are rigidly connected and project through the respective apertures 215 to 218. The locking members 220 to 223 include respective first, second, third and fourth foot members 225, 226, 227 and 228 which project radially inwardly with respect to the cylindrical portion 211 and, in the connected configuration shown in FIGS. 16 to 19, overlay respective cam surfaces 229 to 232 defined by cam formations 233 to 236 of the pump body 203.

Figure 17:
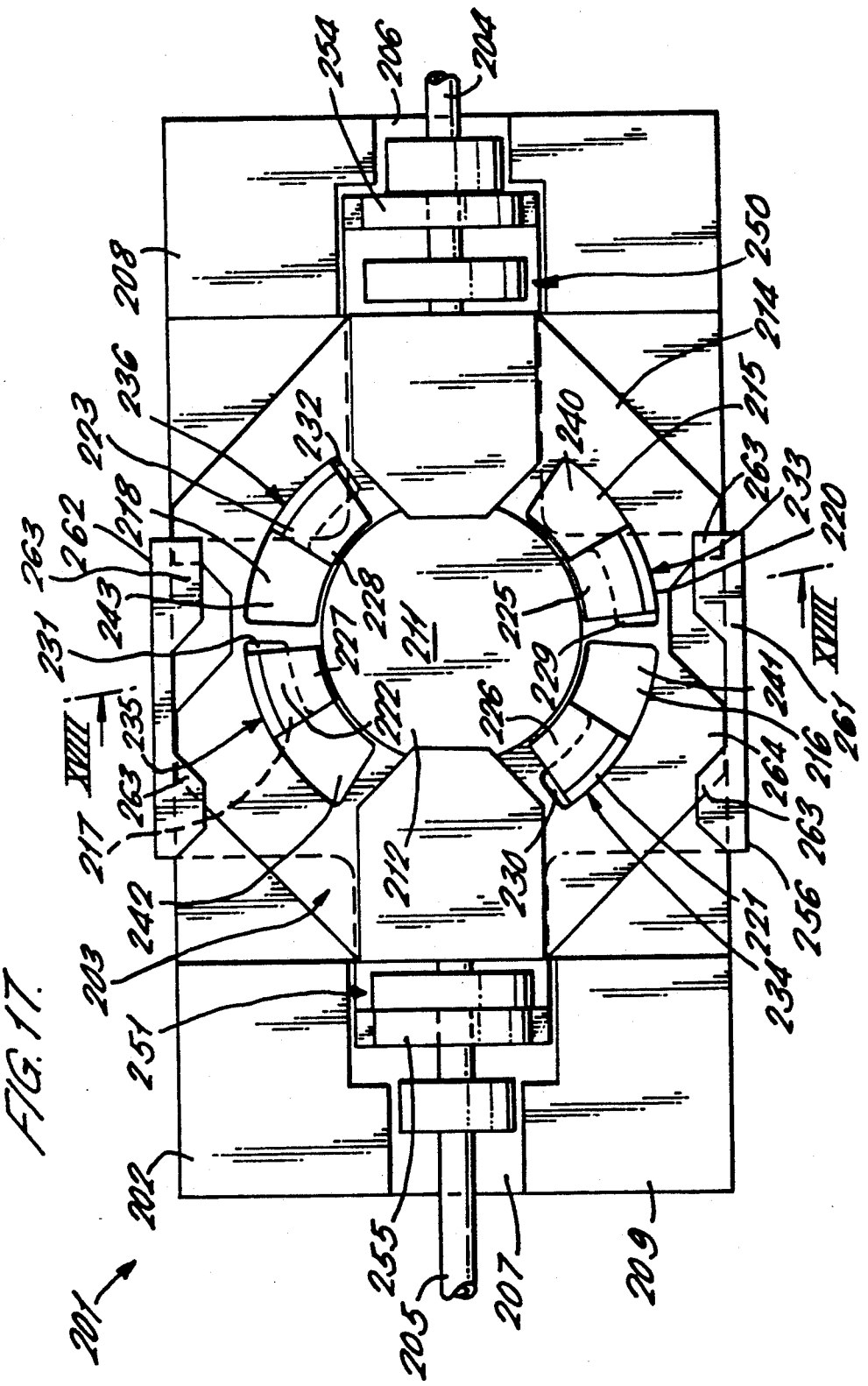
FIG. 17 is a plan view of the pump apparatus of FIG. 16.

The cam surfaces 229 to 232 are ramped relative to the upper surface 214 such that rotation of the mounting member 224 in a clockwise direction as viewed in FIG. 17 results in the foot members 225 to 228 contacting progressively thicker portions of cam formations 233 to 236.

The mounting member 224 is retained in sliding contact with the housing 202 by means of an annular guide 237 as seen in FIG. 18 which has a peripheral groove 238. The mounting member 224 has an annular flange 239 which projects radially inwardly into the groove 238 such that the mounting member is slidable in a circumferential direction relative to the guide 237.

The apertures 215 to 218 include respective enlarged portions 240 to 243 as seen in FIG. 17 which are circumferentially offset from the cam formations 233 to 236 and are of sufficient size to allow the foot members 225 to 228 respectively to pass through the respective apertures 215 to 218.

As shown in FIG. 18 the housing 202 includes a circular piezoelectric transducer 244. The construction of the transducer 244 is shown in greater detail in FIGS. 21 and 22. The transducer 244 comprises a brass disc 245 sandwiched between ceramic wafers 246 of 20 mm diameter.

Upper and lower drive electrodes 270 and 271 are mounted in contact with respective ceramic wafers 246, the drive electrodes comprising metal foils to which drive voltages of appropriate polarity are applied to flex the piezoelectric material of the ceramic wafers. The lower drive electrode 271 is a plane disc and the upper drive electrode 270 includes a radially extending cut-out 272 into which a sense electrode 273 projects. A screening electrode 274 extends intermediate the sense electrode 273 and the upper drive electrode 270 and is connected electrically to the brass disc 245 so as to screen the sense electrode from the drive voltage applied to the upper drive electrode 270.

The radial extent of the sense electrode 273 in a direction towards the centre of the wafer 246 is interrupted by a cut-out 275, the position of which determines the effective length of the sense electrode.

A centrally located boss 247 of a plastics material is bonded to the piezoelectric transducer 244 so as to project in a direction towards the pump body 203.

Figure 20:
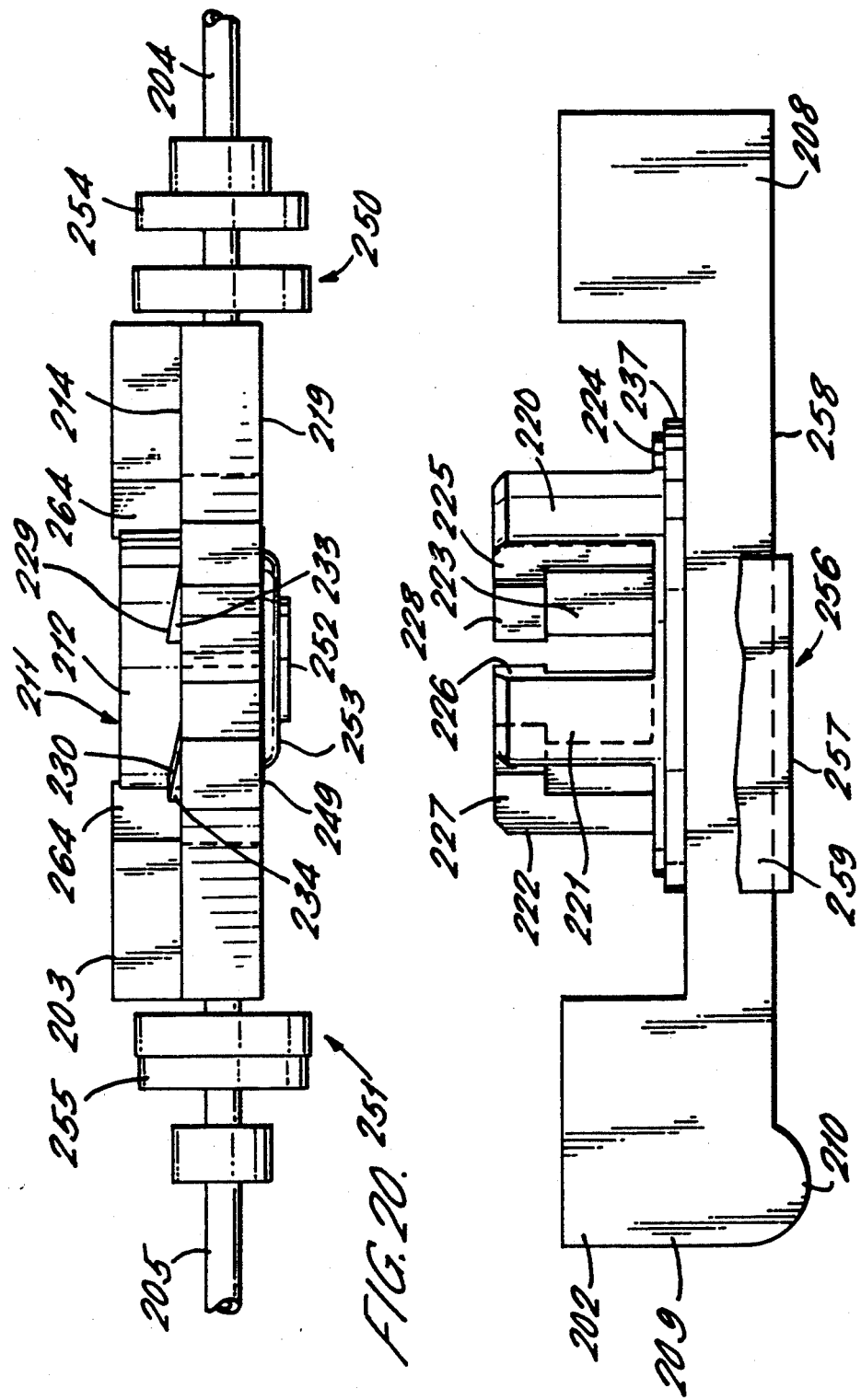
FIG. 20 is a side view of the pump apparatus of FIGS. 16 to 19 with the pump body disconnected from the housing.

The pump body 203 includes a deformable wall 248 which is formed of an elastomeric material. The deformable wall 248 has an annular rim 249 which is bonded to the lower surface 219 of the pump body 203 so as to form a closure to the chamber 213 which is defined between the deformable wall 248 and the rigid wall 212. The inlet and outlet ducts 204 and 205 as seen in FIG. 20 communicate with the chamber 213 for the inlet and outlet of fluid. Inlet and outlet non-return valves 250 and 251 respectively are disposed in the inlet and outlet ducts so as to permit fluid flow in a direction from the inlet duct to the outlet duct.

The deformable wall 248 as seen in FIG. 18 includes a relatively thick central portion 252 which is rigid and a relatively flexible annular membrane portion 253 connected peripherally to the rigid portion, the membrane portion being much thinner than the central portion so as to be resiliently deformable.

The membrane portion 253 is moulded so as to have a shape memory such that the central portion is biassed into a fully extended position as shown in FIG. 20. Displacement of the central portion 252 in a direction towards the rigid wall 212 is accommodated by flexure of the membrane portion 253. As shown in FIG. 18 the central portion 252 is depressed to a partially extended position when the pump body 203 is operatively connected to the housing 202 and in this position the central portion 252 abuts the boss 247 of the piezoelectric transducer 244. The predetermined value for the displacement of the central portion during this depression is 0.3 mm.

Figure 19:
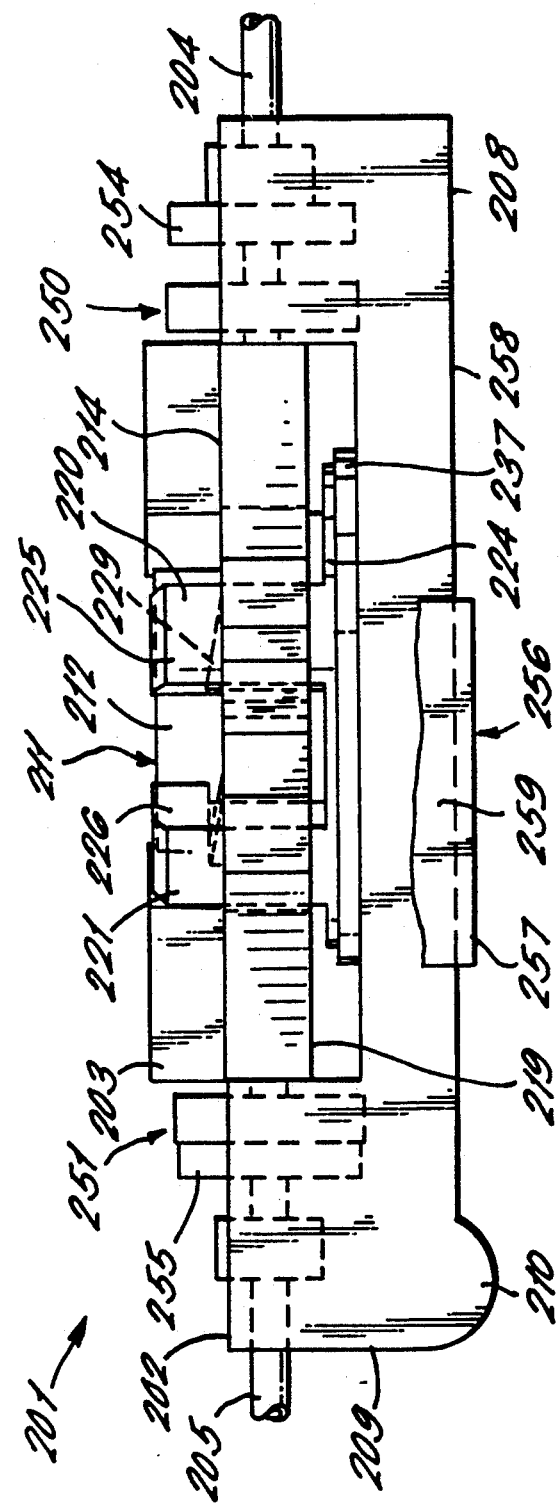
FIG. 19 is a partially sectioned side elevation of the pump apparatus of FIGS. 16 to 18.

The inlet and outlet ducts 204 and 205 as shown in FIG. 19 are provided with annular magnets 254 and 255 through which they respectively extend and the inlet and outlet valves 250 and 251 comprise ferrous valve members (not shown) such that the operation of the valves is dependent on the axial position of the magnets 244 and 245. The housing 202 is provided with a longitudinally slidable handle 256 shown in FIGS. 17, 18 and 20 which, when the housing 202 is connected to the pump body 203, engages the magnets 254 and 255 such that the magnets can be moved between the normal operating position in which the valve members are biassed into contact with respective valve seats (not shown) and a priming position in which both of the valves are held open to permit the free flow of fluid through the pump body.

The handle 256 comprises a base plate 257 shown in FIGS. 18 and 20 which is maintained in sliding contact with a lower surface 258 of the housing 202 and further includes side plates 259 and 260 which project at right angles to the base plate to the level of the upper surface 214 of the pump body. The side plates 259 and 260 include inturned edge portions 261 and 262 respectively seen in FIG. 17 each forming projecting tabs 263 which overlay laterally projecting lugs 264 of the pump body 203 to thereby hold in place the pump body 203 relative to the housing 202 when operatively connected as shown in FIG. 16. When the handle is moved to its priming position (not shown) the tabs 263 interdigitate with the lugs 264 such that the handle no longer holds the pump body in place relative to the housing 202.

In use to commence an infusion of a liquid to a patient, a fresh pump body (supplied in a sterile package) is connected to suitable tubing such that a reservoir of fluid is connected to the inlet duct 204 and a cannulation device is connected to the outlet duct 205. The pump body 203 is oriented such that the outlet duct extends vertically downwards and in this position the magnets 254 and 255 fall under gravity to a priming position in which the inlet and outlet valves 250 and 251 are held opened. The pump body is then primed by allowing fluid to flow through the chamber 213.

After priming the tubing is clamped and the pump body 203 is then presented to the housing 202 as shown in FIG. 20, the pump body 203 and the housing 202 then being brought together so that the locking members 220 to 223 pass through the apertures 215 to 218 respectively. The housing 202 and the pump body 203 are moved together until contact is made between the boss 247 of the piezoelectric transducer 244 and the central portion 252 of the deformable wall 248. The locking members 220 to 223 are then manually rotated relative to the housing 202 in a clockwise direction as viewed in FIG. 16 so that the foot members 225 to 228 are translated circumferentially relative to the cylindrical portion 211 and engage the cam surfaces 229 to 232 respectively.

Continued rotation of the locking members 220 to 223 results in cam action between the cam formations 233 to 236 and the foot members 225 to 228 whereby the pump body 203 is progressively advanced further towards the housing 202. During this further advancement the membrane portion 253 of the deformable wall 248 flexes to accommodate depression of the central portion 252 from its fully extended position to its partially extending position as shown in FIG. 18. The piezoelectric transducer is considerably stiffer than the deformable wall 248 to an extent such that no discernable deflection of the transducer takes place during this further advancement. Because of the shape memory of the membrane portion 253, this depression of the central portion 252 results in the central portion being biassed into positive contact with the piezoelectric transducer 244.

The handle 256 is then longitudinally advanced from its priming position to the normal operating position shown in FIG. 16. In this position the tabs 263 overlay the lugs 264 to positively secure the pump body 203 relative to the housing 202. This movement of the handle 256 also moves the magnets 244 and 245 into their normal operating position in which the inlet and outlet valves 250 and 251 are biassed into their closed positions.

The sliding motion is also sensed by means of a sensor (not shown) to activate the electronic circuitry of the housing 202. Pumping action is then commenced by actuation of the piezoelectric transducer 244 to cyclically flex the transducer towards and away from the chamber 213 with a displacement of ±10 microns. The transducer 244 is actuated by applying drive voltage waveforms of opposite polarities to the upper and lower drive electrodes 270, 271 respectively, pulses of fixed amplitude and variable pulse frequency being applied to the electrodes to produce flexure in alternate directions.

During normal operation an output signal derived from the sense electrode 273 provides a measure of the volume of liquid metered at each actuation of the transducer 244. Over travel or under travel of the transducer 244 resulting from the presence of bubbles in the chamber 213 or the presence of occlusion respectively is detected by comparing the output signal from the sense electrode 273 with respective threshold values.

The amplitude of the sensed voltage from the sense electrode 273 will in general be proportional to the amplitude of flexure of the ceramic wafers 246. Depending on the amplitude of the drive voltage and the frequency of vibration during normal operating conditions, the length of the sensor electrode 273 may require fine tuning to obtain optimum performance. It is for this purpose that the cut-out 275 is provided which effectively allows the length of the sense electrode to be trimmed in this prototype arrangement.

The movement of the transducer 244 is followed precisely by the deformable wall 248 so that the volume of the chamber 213 is cyclically varied to produce pump action.

During the pumping cycle the inlet and outlet valves 250 and 251 function as non-return valves which allow liquid flow only in the direction from inlet duct 204 to outlet duct 205, the valves being opened and closed in response to pressure and suction created in the chamber 213 by movement of the deformable wall 248.

On completion of an infusion the pump body 203 is separable from the housing 202 by moving the handle 256 into its priming position and counter-rotating the locking members 220 to 223 so that the pump body 203 can be lifted from the housing 202. The pump body 203 will typically be discarded as a disposable item and the housing 202 will be reused with further sterile pump bodies in further infusion operations.

The material used for the displaceable wall is carefully selected to provide sufficient flexibility in axial direction to closely follow the motion of the piezoelectric transducer and at the same time provide a biassing force which holds the displaceable wall in contact with the transducer. At the same time the flexible annular membrane portion 253 must have sufficient stiffness to resist ballooning under pressure from the liquid within the chamber. Satisfactory results have been achieved using a thermoplastic polyester elastomer supplied as Hytrel (Trade Mark) Grade 8238 available from Dupont U.K. Ltd., Maylands Avenue, Hemel Hempstead, Hertfordshire HP2 7DP. Other grades of elastomeric material could be used provided suitable adjustment to the dimensions of the membrane are made.

In the above preferred embodiments the thickness of the membrane portion is 0.45 mm.

In the above preferred embodiments the piezoelectric transducer is formed of piezoelectric material of type Sonox P51 obtainable from Hoecht Ceram Tec AG, D.8560 Lauf, P.O. Box 10 02 46, Germany.

Alternative embodiments are envisaged in which the cam means is constituted by cam formations on the locking members in addition to or in place of the cam formations of the pump body.

The inlet and outlet valves may be other than magnetically biassed provided that there are means for holding the valves open in the priming condition.

We claim:

1. A pump apparatus comprising, a pump body defining a pump chamber, an inlet duct communicating between the pump chamber and a source of a liquid to be pumped whereby, in use, the liquid fills the pump chamber, an outlet duct communicating with the chamber for the delivery of the liquid when pumped, actuating means operable to vary the volume of the pump chamber by movement of a flexible wall of the pump chamber to pump the liquid therefrom, the actuating means comprising a composite piezoelectric element having at least one sensor electrode sensing the amplitude of deflection and electronic circuit means operable to energize the piezoelectric element in a pulsed manner, wherein the electronic circuit means includes detection means for comparing the sensed amplitude of deflection with at least one threshold level to provide an indication of abnormal operation of the pump apparatus consistent with occlusion or bubble formation in a volume of the liquid defined by the pump chamber and the inlet and outlet ducts.

2. The pump apparatus as claimed in claim 1, wherein the detection means includes occlusion detection means operable to compare the sensed amplitude of deflection against a lower threshold level and indicating the presence of an occlusion when the sensed amplitude is less than the lower threshold level.

3. The pump apparatus as claimed in claim 1, wherein the detection means includes bubble detection means operable to compare the sensed amplitude of the deflection against an upper threshold level and indicating the presence of a bubble when the sensed amplitude is more than the upper threshold level.

4. The pump apparatus as claimed in claim 1, including flow rate sensing means connected to the electronic circuit means and wherein the circuit means energizes the piezoelectric transducer at a frequency which is variable to maintain the sensed flow rate at a predetermined level.

5. The pump apparatus as claimed in claim 1, comprising electrical circuit means operable to control and energize the piezoelectric element whereby the pump apparatus is self-contained, and wherein the electrical circuit means is located in a housing which is detachable from the pump body and the housing is connected in use to the pump body by a releasable connecting means.

6. The pump apparatus as claimed in claim 5, wherein a transducer comprising the piezoelectric element is located in the housing at a location which overlays the flexible wall of the pump body in use when the housing and pump body are connected in an operable relationship and wherein the apparatus includes wall biassing means biassing the wall into operative engagement with the transducer.

7. The pump apparatus as claimed in claim 6, wherein the wall biassing means comprises an annular membrane portion of the flexible wall connected peripherally to a rigid portion of the flexible wall and having a shape memory such that when the pump body is operatively connected to the housing, the rigid portion is biassed into engagement with the transducer.

8. A pump apparatus comprising, a pump body defining a pump chamber and inlet and outlet ducts communicating with the pump chamber, actuating means operable to vary the volume of the pump chamber by movement of a flexible wall of the pump chamber and first and second valves located in the inlet and outlet ducts respectively, wherein each valve comprises a non-return valve having a valve member movable into and out of engagement with a cooperating valve seat in response to pressure or suction generated in the pump chamber by movement of the wall, magnetic means operable to bias the or at least one of the valve members into a seated position, a piezoelectric transducer being located in a housing at a location which overlays the flexible wall of the pump body in use, when the housing and pump body are connected in an operable relationship, wherein the apparatus includes biassing means for biassing the wall into operative engagement with the transducer, the biassing means comprising an annular membrane portion of the flexible wall connected peripherally to a rigid portion of the flexible wall and having a shape memory such that when the pump body is operatively connected to the housing, the rigid portion is biassed into engagement with the transducer, the body being formed integrally with a reservoir receiving a supply of fluid during use, the reservoir being connected in communication with the inlet duct, wherein the housing includes a reservoir compartment receiving the reservoir when the housing and the body are operatively connected and closure means for closing the reservoir compartment, a priming means being actuated by a manually operated handle mounted on the housing and wherein the handle and the closure means interlock to prevent access to the reservoir compartment when the handle is in a position corresponding to actuating of the priming means to give a normal operating condition of the magnetic means.

9. The pump apparatus as claimed in claim 8, wherein said priming means is selectively operable between a normal operating condition in which the valve biassing means biasses at least one of the valve members into a seated position and a priming condition in which the valve members are biassed by the priming means into an unseated position to allow priming of the pump chamber with fluid.

10. The pump apparatus as claimed in claim 9, wherein the first and second valve members each have a respective ferromagnetic portion and the valve biassing means includes first and second annular magnets through which the inlet and outlet ducts respectively extend, the magnets being held in respective valve seats by the priming means in the normal operating condition and being released therefrom in the priming condition for movement to respective further positions in which the valve members are no longer biassed into a seated position.

11. A pump apparatus comprising, a pump body defining a pump chamber and inlet and outlet ducts communicating with the pump chamber, actuating means operable to vary the volume of the pump chamber by movement of a flexible wall of the pump chamber and first and second non-return valves located in the inlet and outlet ducts respectively, wherein during normal operation conditions, the valves open and close in response to pressure or suction generated in the pump chamber by movement of the wall, the pump apparatus further comprising electrical circuit means operable to control and energize the actuating means comprising a piezoelectric transducer operable to deform the flexible wall of the pump body, the electrical circuit means being located in a housing which is detachable from the pump body and the housing being connected in use to the pump body by a releasable connecting means, wherein the transducer is located in the housing at a location which overlays the flexible wall of the pump body in use, when the housing and pump body are connected in an operable relationship, and wherein the apparatus includes biassing means biassing the wall into operative engagement with the transducer.

12. A method of pumping infusion liquids by means of pump apparatus comprising a pump body defining a pump chamber, an outlet duct communicating with the chamber for the delivery of the liquid when pumped and an inlet duct communicating between the pump chamber and a source of a liquid to be pumped, the method comprising the steps of filling the pump chamber with liquid, operating an actuating means to vary the volume of the pump chamber by movement of a flexible wall of the pump chamber to pump the liquid therefrom, the actuating means comprising a composite piezoelectric element having at least one sensor electrode for sensing the amplitude of deflection, operating an electronic circuit means to energize the piezoelectric element in a pulsed manner, sensing the amplitude of deflection and comparing the sensed amplitude of deflection with at least one threshold level to provide an indication of abnormal operation of the pump apparatus consistent with occlusion or bubble formation in a volume of the liquid defined by the pump chamber and the inlet and outlet ducts.

13. A method as claimed in claim 12, including the step of comparing the sensed amplitude of deflection against a lower threshold level and indicating the presence of an occlusion when the sensed amplitude is less than the lower threshold level.

14. A method as claimed in claim 12, including the step of comparing the sensed amplitude of the deflection against an upper threshold level and indicating the presence of a bubble when the sensed amplitude is more than the upper threshold level.

15. A method as claimed in claim 12, including operating a flow rate sensing means connected to the electronic circuit means and wherein the circuit means energizes the piezoelectric transducer at a frequency which is variable to maintain the sensed flow rate at a predetermined level.

16. A method as claimed in claim 12, wherein the pump apparatus is self-contained and wherein the electrical circuit means is located in a housing which is detachable from the pump body, the method including the step of connecting the housing in use to the pump body by a releasable connecting means.

17. A method as claimed in claim 16, wherein a transducer comprising the piezoelectric element is located in the housing at a location which overlays the flexible wall of the pump body in use, the method including the step of biassing the wall into operative engagement with the transducer when the housing and pump body are connected in an operable relationship.

18. A method as claimed in claim 17, wherein the wall is biassed into operative engagement with the transducer by means of an annular membrane portion of the flexible wall being connected peripherally to a rigid portion of the flexible wall and having a shape memory such that when the pump body is operatively connected to the housing, the rigid portion is biassed into engagement with the transducer.

19. A method of pumping infusion liquids by means of pump apparatus comprising a pump body defining a pump chamber with inlet and outlet ducts communicating with the pump chamber, and first and second non-return valves located in the inlet and outlet ducts respectively, the method comprising the steps of varying the volume of the pump chamber by movement of a flexible wall of the pump chamber whereby during normal operation conditions the valves open and close in response to pressure or suction generated in the pump chamber by movement of the wall, the pump apparatus further comprising electrical circuit means operable to control and energize a piezoelectric transducer operable to deform the flexible wall of the pump body, the electrical circuit means being located in a housing which is detachable from the pump body, the method including the steps of connecting the housing to the pump body by a releasable connecting means, such that the transducer is located in the housing at a location which overlays the flexible wall of the pump body and biassing the wall into operative engagement with the transducer.

20. Pump apparatus comprising a pump body defining a pump chamber, a displaceable wall of the pump body being displaceable to vary the volume of the pump chamber, biassing means biassing the displaceable wall into a fully extended position in which the volume of the chamber is maximised, a housing, connecting means releasably connecting the housing to the pump body the housing comprising a piezoelectric transducer operable to reciprocatingly move the displaceable wall when the housing and the pump body are connected, wherein the connecting means comprises cam means operable between the pump body and the housing during connection of the pump body to the housing to move the pump body from a first position relative to the housing in which the displaceable wall is in its fully extended position in abutment with the transducer and a second position relative to the housing in which the displaceable wall is partially extended in its normal operating position whereby the displaceable wall is biassed into contact with the transducer by action of the biassing means such that contact is maintained during reciprocation of the transducer.

21. Pump apparatus as claimed in claim 20 wherein the connecting means comprises at least one locking member connected to the housing and movable between an unlocked position and a locking position in which a foot portion of the locking member overlays a contact surface of the pump body so as to prevent disconnection of the pump body from the housing.

22. Pump apparatus as claimed in claim 21 wherein at least one of the foot portion and the contact surface comprises a ramped surface such that movement of the locking member into the locking position provides cam action whereby the foot portion and the contact surface together constitute the cam means.

23. Pump apparatus as claimed in claim 21 comprising a plurality of locking members which are peripherally spaced relative to the displaceable wall, the locking members being mounted on a mounting member so as to be movable in unison between their respective locking and unlocked positions.

24. Pump apparatus as claimed in claim 23 wherein the mounting member comprises an annular flange and the housing further comprising annular guide means cooperating with the flange to facilitate axial rotation of the annular flange between positions corresponding to the unlocked and locking positions of the locking members.

25. Pump apparatus as claimed in claim 21 wherein the pump body is provided with at least one aperture through which a cooperating locking member extends when the housing is connected to the pump body.

26. Pump apparatus as claimed in claim 20 wherein the displaceable wall is formed of an elastomeric material and includes a relatively thick central portion which is relatively rigid and a relatively flexible annular membrane portion connected peripherally to the rigid portion, the membrane portion having a shape memory such that the central portion is biassed into the fully extended position to thereby constitute the biassing means.

27. A disposable pump body for use in cooperating engagement with a housing having a piezoelectric transducer, the pump body defining a pump chamber, a displaceable wall of the pump body being displaceable to vary the volume of the pump chamber, biassing means biassing the displaceable wall into a fully extended position in which the volume of the chamber is maximised, connecting means operable in use to releasably connect the housing to the pump body such that the displaceable wall is partially extended in its normal operating position and is biassed into contact with the transducer by action of the biassing means wherein the displaceable wall is formed of an elastomeric material and includes a relatively thick central portion which is relatively rigid and a relatively flexible annular membrane portion connected peripherally to the rigid portion, the membrane portion having a shape memory such that the central portion is biassed into the fully extended position to thereby constitute the biassing means.

28. A transducer for use in an infusion pump apparatus comprising a wafer of piezoelectrically active material, a drive electrode bonded to a first major face of the wafer, a ground electrode bonded to a second major face of the wafer, the drive electrode being provided with a cut-out revealing an elongate exposed portion of the wafer, a sense electrode bonded to the exposed portion and a screening electrode bonded to the exposed portion at a location intermediate the sense electrode and the drive electrode, the screening electrode being electrically connected to the ground electrode in use to provide electromagnetic screening of the sense electrode from a drive voltage applied to the drive electrode, whereby the sense electrode is operable to produce a signal representative of deflection of the wafer.

* * * * *